United States Patent
Yung et al.

(10) Patent No.: US 9,156,037 B2
(45) Date of Patent: Oct. 13, 2015

(54) MICROFLUIDIC DEVICE AND USES THEREOF

(75) Inventors: Chong Wing Yung, San Jose, CA (US);
Donald E. Ingber, Boston, MA (US);
Jason O. Fiering, Boston, MA (US);
Mathew Varghese, Sunnyvale, CA (US)

(73) Assignees: Children's Medical Center Corporation, Boston, MA (US); The Charles Stark Draper Laboratory, Inc., Cambridge, MA (US)

(*) Notice: Subject to any disclaimer, the term of this patent is extended or adjusted under 35 U.S.C. 154(b) by 1004 days.

(21) Appl. No.: 13/144,572

(22) PCT Filed: Jan. 15, 2010

(86) PCT No.: PCT/US2010/021195
§ 371 (c)(1),
(2), (4) Date: Feb. 29, 2012

(87) PCT Pub. No.: WO2010/123594
PCT Pub. Date: Oct. 28, 2010

(65) Prior Publication Data
US 2012/0149021 A1    Jun. 14, 2012

Related U.S. Application Data

(60) Provisional application No. 61/144,897, filed on Jan. 15, 2009.

(51) Int. Cl.
*C12Q 1/68*    (2006.01)
*B03C 1/01*    (2006.01)
(Continued)

(52) U.S. Cl.
CPC . *B03C 1/01* (2013.01); *B03C 1/288* (2013.01); *G01N 33/54326* (2013.01); *G01N 33/54366* (2013.01); *B03C 2201/18* (2013.01); *G01N 1/40* (2013.01)

(58) Field of Classification Search
USPC .................. 435/6.12, 287.1, 287.2
See application file for complete search history.

(56) References Cited

U.S. PATENT DOCUMENTS 5,236,824 A    8/1993    Fujiwara et al.
5,270,199 A    12/1993    Ezekowitz
(Continued)

FOREIGN PATENT DOCUMENTS

WO    2010/123594    10/2010
WO    2011/090954    7/2011
(Continued)

OTHER PUBLICATIONS

Inglis, et al. "Continuous microfluidic immunomagnetic cell separation" Applied Physics Letters 85(21):5093 (2004).
Blankenstein, "Microfabricated flow system for magnetic cell and particle separation" Scientific and Clinical Applications of Magnetic Carriers, ed. W.S. U. Hafeli J. Teller, and M. Zborowski, 1997, New York: Plenum Press, 233-245.
Chang et al., "Crystallization and preliminary x-ray analysis of a trimeric form of human mannose binding protein" J. Mol. Biol., 1994, 5: 241(1):125-127.
(Continued)

*Primary Examiner* — Kenneth Horlick
(74) *Attorney, Agent, or Firm* — Nixon Peabody LLP

(57) ABSTRACT

A microfluidic device for separating target components from a source fluid includes one or more source channels connected to one or more collection channels by one or more transfer channels. The target components of the source fluid can be magnetic or bound to magnetic particles using a know binding agent. A source fluid containing magnetically bound target components can be pumped through the source channel of the microfluidic device. A magnetic field gradient can be applied to the source fluid in the source channel causing the magnetically bound target components to migrate through the transfer channel into the collection channel. The collection channel can include a collection fluid that is stagnant until a predefined volume of source fluid is processed or a predefined volume of target components accumulate in the collection channel, at which point collection fluid can be pumped into the collection channel to flush the target components out of the collection channel. The target components can be subsequently analyzed for detection and diagnosis.

20 Claims, 8 Drawing Sheets

(51) Int. Cl.
  *B03C 1/28* (2006.01)
  *G01N 33/543* (2006.01)
  *G01N 1/40* (2006.01)

(56) References Cited

U.S. PATENT DOCUMENTS

| | | | |
|---|---|---|---|
| 6,241,894 | B1 | 6/2001 | Briggs et al. |
| 6,432,630 | B1 | 8/2002 | Blankenstein |
| 6,541,213 | B1 | 4/2003 | Weigl et al. |
| 6,846,649 | B1 | 1/2005 | Thiel et al. |
| 6,875,855 | B1 | 4/2005 | Roberts et al. |
| 7,138,269 | B2 * | 11/2006 | Blankenstein ............ 435/287.2 |
| 7,150,834 | B2 | 12/2006 | Mueth et al. |
| 7,276,170 | B2 | 10/2007 | Oakey et al. |
| 7,807,454 | B2 * | 10/2010 | Oh et al. ................... 435/308.1 |
| 2002/0036141 | A1 | 3/2002 | Gascoyne et al. |
| 2003/0129676 | A1 | 7/2003 | Terstappen et al. |
| 2004/0018611 | A1 | 1/2004 | Ward et al. |
| 2004/0229212 | A1 | 11/2004 | Thiel et al. |
| 2005/0059041 | A1 | 3/2005 | Johnson et al. |
| 2005/0061962 | A1 | 3/2005 | Mueth et al. |
| 2005/0121604 | A1 | 6/2005 | Mueth et al. |
| 2005/0274650 | A1 | 12/2005 | Frazier et al. |
| 2006/0223178 | A1* | 10/2006 | Barber et al. ................ 435/325 |
| 2009/0047297 | A1 | 2/2009 | Kim et al. |
| 2009/0078614 | A1 | 3/2009 | Varghese et al. |
| 2009/0220932 | A1 | 9/2009 | Ingber et al. |
| 2010/0044323 | A1 | 2/2010 | Asplund et al. |

FOREIGN PATENT DOCUMENTS

| | | | |
|---|---|---|---|
| WO | 2012100099 | A2 | 7/2012 |
| WO | 2013/012924 | | 1/2013 |

OTHER PUBLICATIONS

Chang et al., Langmuir., 22(4):1459-68 (2006). "Evaporation-induced particle microseparations inside droplets floating on a chip."
Courbin, L., et al. "Imbibition by polygonal spreading on microdecorated surfaces" Nature Materials, 2007, 6:661-664.
Jung et al., Langmuir, 18(16), pp. 6133-6139 (2002). "Perfluorinated Polymer Monolayers on Porous Silica for Materials with Super Liquid Repellent Properties."
Kim, P. et al., "Structural Transformation by Electrodeposition on Patterned Substrates (STEPS): A New Versatile Nanofabrication Method" Nano Letters, in press (2011).
Mach, "Continuous scalable blood filtration device using inertial microfluidics" Biotechnol Bioeng, 107(2):302-11 (2010).
Porter et al., "An evaluation of lectin-mediated magnetic bead cell sorting for the targeted separation of enteric bacteria" Journal of Applied Microbiology, 84(5):722-32 (1998).
Rowley et al., "Isolation of CD34+ cells from blood stem cell components using the Baxter Isolex system" Bone Marrow Transplant, 21:1253-62 (1998).
Sung et al., Biomed Microdevices. 11(4):731-8 (2009). "Prevention of air bubble formation in a microfluidic perfusion cell culture system using a microscale bubble trap."
Wenzel, R.N. "Resistance of solid surfaces to wetting by water" Ind. Eng. Chem. 1936, 28:988-994.
Wong et al., Bioinspired self-repairing slippery surfaces with pressure-stable omniphobicity Nature, 2011, 477:443-447.
Xia et al., "Combined microfluidic micromagnetic separation of living cells in continuous flow" Biomed Microdevices, 8 (4):299-308 (2006).
Yung et al., Lab on a Chip, 9:1171-1177 (2009). "Micromagnetic-microfluidic blood cleansing device."

* cited by examiner

MICROFLUIDIC DEVICE AND USES THEREOF

CROSS-REFERENCE TO RELATED APPLICATIONS

This application is a 35 U.S.C. §371 National Stage Entry Application of International Application No. PCT/US2010/021195, filed Jan. 15, 2010, which designates the U.S., and which claims benefit under 35 U.S.C. §119(e) of U.S. Provisional Patent Application Ser. No. 61/144,897 filed on Jan. 15, 2009, the contents of which are incorporated herein by reference in their entirety.

GOVERNMENT SUPPORT

The subject matter described herein was made with support under grant number No. W81XWH-05-1-0115 awarded by the United States Department of Defense. The United States government has certain rights in the claimed subject matter.

REFERENCE TO MICROFICHE APPENDIX

Not Applicable

BACKGROUND

1. Technical Field of the Invention

The present invention is directed to fluidic devices that can be used to separate target components from flowing fluids. More specifically, the invention is directed to methods for and systems using fluidic and microfluidic devices to separate particulate, molecular and cellular material from a flowing fluid.

2. Description of the Prior Art

Chemical and biological separation and concentration has historically included methods such as solid-phase extraction, filtration chromatography, flow cytometry and others. Known methods of magnetic separation in biological fields include aggregation in batches, capture on magnetized surfaces, and particle deflection (or "steering") in single-channel devices. Typically, the particle of interest is chemically bound to magnetic microparticles or nanoparticles.

Existing methods are typically batch processes rather than continuous free-flow processes. This limits their usefulness in in-line systems. Moreover, existing methods typically operate at the macroscale, where diffusion distances require slower flow speeds, resulting in limited throughput. This problem is compounded in single-channel devices. The present invention improves on known methods and apparatuses for magnetic separation of particles from a fluid by providing a continuous, free-flow, higher throughput separation.

Published US Patent Application No. 2009-0220932 to Ingber, et al. and published US Patent Application No. 2009-0078614 to Varghese et al, both of which are hereby incorporated by reference in their entirety, disclose fluid separation devices and methods for separating particles from a flowing fluid. These devices and methods involve directing an input fluid, containing target particles, and a collection fluid into a common microfluidic channel. The input fluid and the collection fluid flow side-by-side through the microfluidic channel and a magnetic field is used to pull magnet target particles or target particles bound to target particles from the input fluid to the collection fluid before the input fluid and the collection fluid are separated and directed through separate outlets.

SUMMARY

The present invention is directed to a microfluidic device that facilitates the separation and removal of target components from a source fluid flowing in a source microfluidic channel without removing or altering other components in the source fluid. The fluid can be a liquid or a gas. The target components can be any particulate, molecule or cellular material that is magnetic or can be bound to a magnetic particle introduced to the flowing fluid. The source channel(s) can be connected to a collection microfluidic channel(s) by one or more transfer channels. A collection fluid, flowing in the collection channel(s) can be used to flush the target components out of the microfluidic device. A magnet or a magnetic source can be positioned adjacent the collection channel, or an external magnetic field gradient can be applied, to attract the magnetic target components or the target components bound to a magnetic particle into the transfer channels and into the collection channel(s) where they can be carried away in the collection fluid. The magnet or the magnetic field gradient source can be positioned relative to the collection channel(s) to permit the magnetic field gradient to draw the target components into the transfer channels and the collection channel, but not so strong as to cause the target components to lodge in the collection channel(s), unable to be flushed out by the flow of the collection fluid. As one of ordinary skill would appreciate, the position of the magnet or the source of the magnetic field gradient (in the case of an electromagnet) relative to the channels can be determined as a function of any or all of the following: the strength of the magnetic field and field gradient, the magnetic properties of the magnetic particles, the size of the target components and/or the magnetic particles, the size and/or shape of the channels, or the speed and/or viscosity of the fluids used.

In operation, the source fluid can be pumped into the source channel(s) and the magnet field gradient is applied to the source fluid as it flows through the source channel. Pumping can be achieved using a powered or manual pump, centripetal or gravitational forces. The magnetic field that is generally applied in a direction perpendicular to the direction of fluid flow applies additional forces on the target components carried by the source fluid flowing through the source channel(s) causing the magnetic target components and/or the magnetically bound target components to travel into the transfer channels and eventually become drawn into the parallel collection channel. In accordance with the invention, the magnet field gradient can apply attraction forces or repulsion forces on the magnetic particles or the magnetic target components to cause them to flow into a transfer channel.

BRIEF DESCRIPTION OF THE DRAWINGS

The accompanying drawings illustrate an embodiment of the invention and depict the above-mentioned and other features of this invention and the manner of attaining them. In the drawings.

DESCRIPTION OF THE INVENTION

The present invention is directed to a fluidic device that facilitates the separation and removal of target components from a source fluid flowing in a source channel without removing or altering other components in the source fluid. The fluid can be a liquid or a gas. The target components can be any particulate, molecule or cellular material that is magnetic or can be bound to a magnetic particle introduced to the flowing fluid. Multiple fluidic devices can be coupled together in series and/or parallel to improve the throughput and efficiency of the system. The target components are collected in a collection fluid that can be further processed to analyze the target components. The collection fluid containing target components can be collected in a reservoir and batch techniques, such as immunostaining, culturing, polymerase chain reaction (PCR), mass spectrometry and antibiotic sensitivity testing can be used to analyze the target components for use in diagnosis. Alternatively, the collection fluid containing the target components can be directed into an inline or on-chip diagnostic or analysis device that can process the target components as they flow with the collection fluid. Because target components are either magnet or bound to magnetic particles, magnetic field gradients can be used to collect the target components for inline or on-chip analysis or direct the target components to other devices for detection or analysis.

Figure 1:
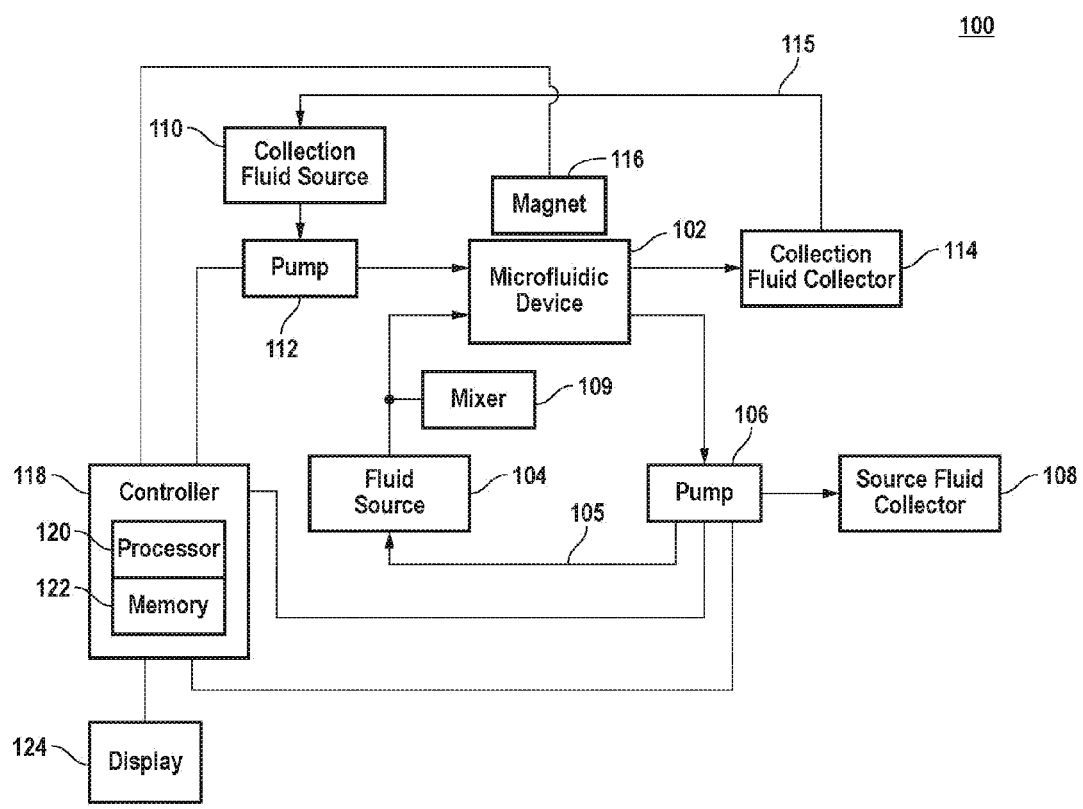
FIG. 1 shows a block diagram of an overall system according to the invention.

FIG. 1 illustrates a block diagram of an overall system incorporating the microfluidic device 102 in accordance with an aspect of the present invention. In particular, the system 100 can include one or more microfluidic devices 102. It should be noted that although only one device 102 is shown in FIG. 1, more than one device 102 can be utilized as part of a system in which multiple microfluidic devices 102 can be connected to one another in serial and/or parallel fashion. Alternatively, multiple microfluidic devices 102 can be employed in a system whereby each microfluidic device 102 can be separately or individually connected between one or more fluid source(s) 104 and one or more fluid collector(s) 108.

The system in FIG. 1 can include one or more source fluid sources 104 and be configured to pump the source fluid to the microfluidic device 102. The source fluid can include, but is not limited to, blood, including cord blood, serum, plasma, urine, liquefied stool sample, cerebrospinal fluid, amniotic fluid, lymph, mucus, tears and/or sputum, as well as biologically or pharmaceutically acceptable fluids, such as saline, buffers, physiological salt solutions or various cell culture media or any fluid containing particulates to be removed. As will be discussed in more detail below, a biofluid sample is preferably the fluid which is to be cleansed, or contains cells or molecules which are to be isolated and removed there from. The fluid source 104 can be a human or animal, wherein the blood and/or other fluids are taken directly from the human or animal. The fluid source 104 can also be the source of a non-biofluid, such as a contaminated water supply, a liquefied food source, or any fluid (liquid or gas) that can benefit from the removal of particulates or components. This can include, for example, removing contaminants from water, cleaning petroleum based lubricants and removing particulate emissions from combustion exhaust gases.

After removal of the desired target component, the "cleansed" fluid material and/or the collection fluid containing the target components can be transferred for further processing, such as detection or analysis. In some embodiments of the invention, the cleansed fluid can returned to the source. In the case of biofluids, the cleansed biofluid can be returned to the originating biological system, or to another subject or to a culture medium, biological scaffold, bioreactor, or the like. In some embodiments, it can be desirable to subject the cleansed biofluid to post processing, for example, further treatment, filtering or a (blood) warming process prior to being returned to the originating biological system.

In accordance with one embodiment of the invention, a mixing component 109, such as a low-shear mixer or magnetic agitator, can be used to inject and mix magnetic particles (e.g., paramagnetic or superparamagnetic beads) with the source fluid prior to entering the microfluidic device 102. In accordance with one embodiment of the invention, a low-shear mixer can be used to mix magnetic particles developed by conjugating antibodies to the surface of 1 μm diameter paramagnetic beads (DYNAL® magnetic beads, Invitrogen, Carlsbad, Calif.; DYNABEADS MYONE™ magnetic beads, Invitrogen), sometimes referred to a "magnetic opsonins" into the source fluid prior to entering the microfluidic device. In the particular case of sepsis therapy, contaminated whole blood is continually drawn from a patient via a catheter placed into a peripheral vein, which is heparinized, and directed into the low-shear blood mixer 109. Magnetic particles are then continually infused into the mixer 109 at an optimized rate (e.g. ensuring a ratio of 120 beads to every *C. albicans* fungal cell). At this stage, the magnetic particles will selectively bind to the pathogens in the blood through their surface antibody coating and confer magnetic mobility only to these targeted cells. The same approach can be used with generic opsonins, such as complement proteins or mannose-binding lectin, to bind unknown pathogens in blood or other biological fluids. As the contaminated blood flows from the mixer 109 into the microfluidic device 102, the low aspect ratio of the microfluidic channel effectively flattens out the geometry of the biofluid to maximize the area of exposure to the magnetic field gradients, as well as to minimize the distance that magnetically bound pathogens need to reach the transfer channels on their way to the collection channel. The transfer channels and source fluid channel(s) can be pre-filled with the collection fluid, such as saline, although other compatible fluids, such as the collection fluids described herein can also be used.

As shown in FIG. 1, one or more pumps 106 can be connected to the microfluidic device 102 causing the fluid to flow through the microfluidic device 102. It should be noted that although the pump 106 is shown downstream from the microfluidic device 102, a pump 106 can be additionally/alternatively located upstream from the microfluidic device 102. In one embodiment, the pump 106 can be connected to one or more source fluid collectors 108 where some or all of the exit fluid is collected and stored. In one embodiment where the source fluid is a biofluid, the biofluid that passes through the microfluidic device 102 can be returned to the human or animal from where the biofluid was taken. Additionally or alternatively, the pump 106 can be connected to the fluid source 104 (via line 105), whereby the exiting fluid can be recirculated to the fluid source 104 to be processed by the microfluidic device 102. The pump 106 can be an electronic, automatically-controlled pump or a manually-operated pump. Alternatively, the fluid source can be elevated to allow gravity to push, with or without the assistance of a pump, the source fluid through the microfluidic device 102. The microfluidic system 100 can include one or more flow valves 103, 107 connected at the inlet and/or the outlet of the microfluidic device 102 to allow the flow of the source fluid to be stopped, for example, during the time when the collection fluid flows through the collection channel.

In one embodiment, the microfluidic device 102 can also be connected to one or more collection fluid sources 110 which supply the collection fluid to the microfluidic device 102. In an embodiment, one or more pumps 112 can be connected to the collection fluid source 110 to supply the collection fluid to the microfluidic device 102. It should be noted that, as with pump 106, one or more pumps 112 can be additionally/alternatively located downstream from the microfluidic device 102 instead of upstream, as shown in FIG. 1. It should also be noted that the pump 112 is optional and a syringe or other appropriate device (or gravity) can be used to drive the collection fluid through the microfluidic device 102 to the collection fluid collector 114 or an inline analysis or detection device.

In one embodiment, the microfluidic device 102 can be connected to a collection fluid collector 114, whereby exiting collection fluid is stored in the collector 114. Additionally or alternatively, the collector 114 can be connected to the collection fluid source 110 (via line 115), whereby the exiting collection fluid can return to the collection fluid source 110 to be recirculated through to the microfluidic device 102. Prior to returning the collection fluid to the collection fluid source 110, the collection fluid can be processed to remove the magnetically bound target components, such as by filtering or using magnetic separating techniques.

As shown in FIG. 1, one or more magnetic sources 116, such as rare earth magnets or electromagnets, can be positioned proximal to the microfluidic device 102. The magnets 116 aid in removing magnetic particles that are attached to target cells or molecules in the source fluid, as discussed herein.

The system 100 can also include one or more controllers 118 coupled to one or more of the components in the system. The controller 118 preferably includes one or more processors 120 and one or more local/remote storage memories 122. A display 124 can be coupled to the controller 118 to provide a user interface to control the operation of the system and display resultant, operational and/or performance data in real time to the user. The controller 118 can be optionally connected to pump 106 and/or pump 112 to individually or collectively control operational parameters of these components, such the flow rates and/or initiating and terminating flow of the respective fluids in and out of the microfluidic device 102. Optionally, the controller 118 can be connected to the fluid sources 104, 110, the valves 103, 107, the mixer component 109 and/or the collectors 108, 114 to operate valves in these components and/or to selectively dispense respective fluids or magnetic beads in a controlled manner within the system. Optionally, the controller 118 can be connected to the one or more magnetic sources 116 to selectively control power, voltage and/or current supplied to the magnetic sources 116 to control and adjust the magnetic field gradients in order to control the performance of the microfluidic device 102. It is also possible for the controller 118 to selectively position and control the force levels of the magnet field gradients at desired distances with respect to the microfluidic device 102 to selectively control the magnetic field gradient applied to the channels of the microfluidic device 102. Although not shown, the controller 118 can be connected to various sensors in the microfluidic device 102 and/or other components in the system 100 to monitor and analyze the behavior and interaction of the fluids and/or target components traveling in the system 100. The controller 118 can be a personal computer including software and hardware interfaces connected to the pumps, valves and sensors to control the operation of the system 100. Alternatively, controller 118 can be dedicated micro controller specifically designed or programmed with dedicated software to interface with the pumps, valves and sensors to control the system 100. It should be noted that the system shown in FIG. 1 is exemplary and that additional, other or less components may be employed without departing from the inventive concepts herein.

Figure 2A:
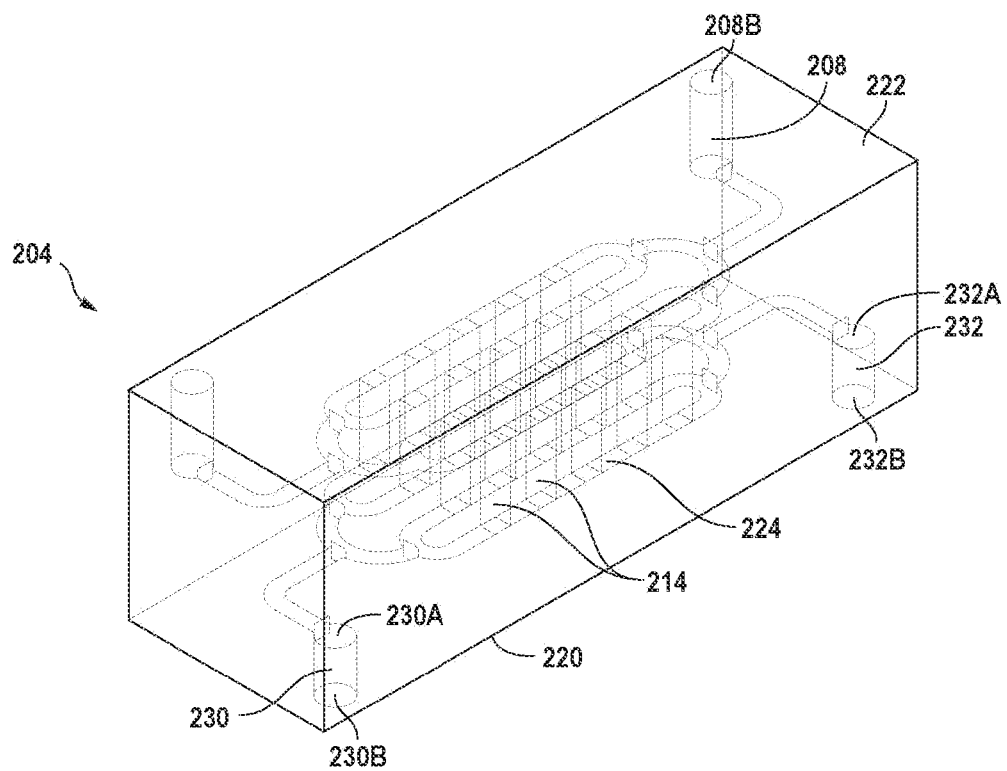
FIGS. 2A-2D show various views of a fluidic device according to the invention.

FIGS. 2A, 2B, 2C and 2D show various views of a microfluidic device in accordance with the present invention. FIG. 2A shows the microfluidic device in accordance with an embodiment of the present invention. The microfluidic device 102 shown in FIGS. 2A, 2B, 2C and 2D can include a rectangular body, although other shapes can be used (e.g. circular, elliptical, trapezoidal and the like). As shown in FIG. 2A, the microfluidic device 102 can include one or more source channels 224 extending between one or more inlet ports 230 and one or more outlet ports 232. The source channels 224 can be rectangular in cross-section although other polygonal, non-polygonal, circular, or oval cross-sectional shapes can be used.

The source fluid containing the target components flows into the source channels 224 through one or more inlet ports 230 and exits from the microfluidic device 102 through one or more outlet ports 232. It should be noted that the source fluid channels 224 can extend along the length of the microfluidic device 102 (e.g. the y-direction), as shown in FIGS. 2A, 2B, 2C and 2D. Inlet port 230 and outlet port 232, while shown oriented perpendicular (i.e. along the z-direction) to the source fluid channels 224, can be oriented in any angle (including straight through) with respect to the source fluid channels 224.

Figure 2B:
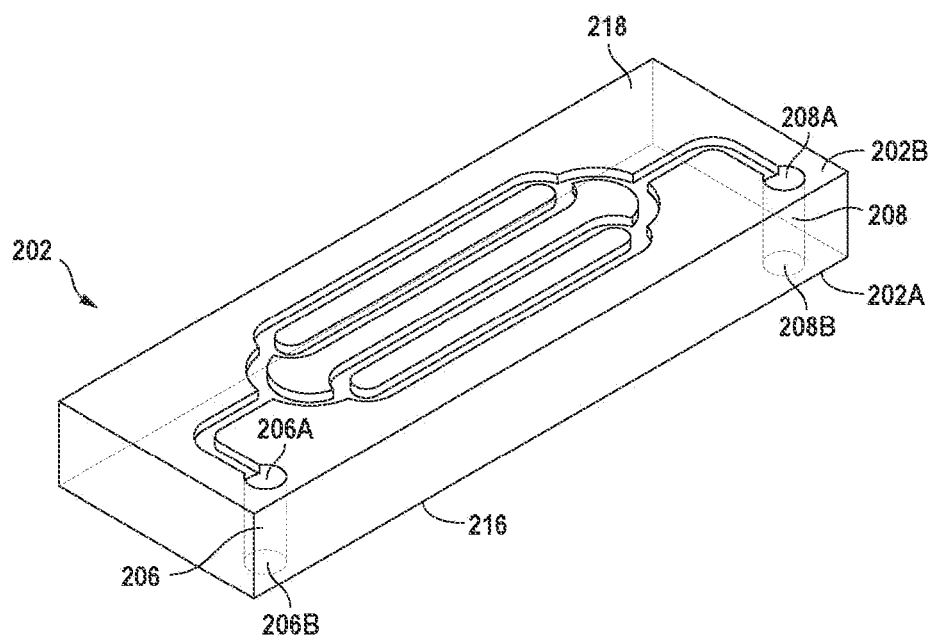
Figure 2C:
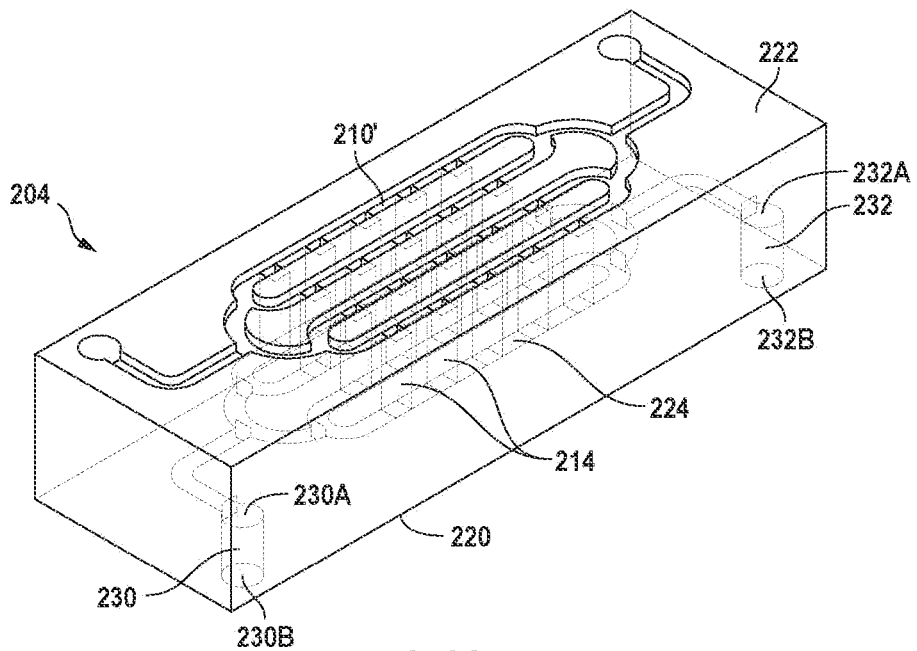

The cross-sectional dimension of the individual source fluid channels 224 can be designed to more effectively expose the target components to the magnetic field and guide the attracted target components toward the transfer channels 214. In one embodiment, the source fluid channels 224 can have a flattened geometry in order to maximize the area of exposure to the magnetic fields. In addition, the source fluid channels 224 can be designed to slow the flow rate of the source fluid as it passes through the source channels 210 to maximize the number of magnetically bound target components to migrate into the transfer channels 214. In one preferred embodiment, the source channels 224 for transporting biofluid can be 2 cm long by 2 mm wide by 0.16 mm high and the collection channels 210 for transporting collection fluid can be 2 cm long by 2 mm wide by 0.08 mm high In addition, the microfluidic device 102 can include one or more collection channels 210 which can run along the length of the microfluidic device 102, parallel to the source channels 224. The collection channels 210 can be rectangular in cross-section although other polygonal, non-polygonal, circular or oval cross-sectional shapes can be used. The collection channels 210 can extend between one or more inlet ports 206 and one or more outlet ports 208. The collection channels 210 can extend along the length of the microfluidic device 102 (e.g. in the y-direction), as shown in FIGS. 2A, 2B, and 2C. The inlet port 230 and outlet port 232, while shown oriented perpendicular to the collection fluid channels 210, can be oriented in any angle (including straight through) with respect to the collection fluid channels 210.

The collection fluid can flow at the same or different flow rates compared to the source fluid or biofluid. The collection fluid can also flow periodically, where it cycles from stagnant to flowing compared to the source fluid or biofluid. In addition, the pressure applied to the collection fluid in the microfluidic device 102 can be controlled to prevent the mixing or loss of the source biofluid. For example, the collection fluid can be maintained at a lower pressure than the source fluid to prevent the collection fluid from entering the transfer channels 214 and mixing with the source fluid. Alternatively, the collection fluid, being compatible with the source fluid (e.g., a biocompatible fluid such as an injectable saline solution), can be maintained at a higher pressure than the source fluid allowing some collection fluid to enter the transfer channels 214 to prevent the entry and loss of the source fluid into the collection channel 210. In one embodiment and as described further below, the flow of the collection fluid can be cycled between flowing and stagnant or nearly stagnant. For example, the collection fluid can be stationary or stagnant and maintain a relatively high pressure for a period of time sufficient for target components to accumulate in the collection channels 210 and/or the transfer channels 214 and, when a determined amount of target components have accumulated (e.g., as a function of time or volume), the collection fluid can be cycled into the flowing state at the same pressure to flush out the target components and replace the collection channel(s) 210 with cleaner collection fluid without altering the remaining source fluid. The periodic flushing operation can lower the pressure in the collection channels 210 to draw the fluid in the transfer channels into the collection channels 210 to facilitate flushing of the target components. During the flushing operation, the source fluid can be stopped, stagnant, or nearly stagnant to minimize or prevent the loss of source fluid into the transfer channel 214 and/or the collection channel 210.

In an alternative embodiment, the system 100 can include sensors that monitor the migration of the target components through the transfer channel 214 into the collection channel 210 in order to determine how to control the flow in the collection channel 210 remove the accumulated target components. The sensor can be one or more optical sensors that detect the accumulation of target components as they block light projected through the transfer channel or the collection channel onto the sensor or detect light reflected by target components. The optical detector can be a simple photodiode or a more complex imaging device, such as a CCD based camera. When the sensor detects that a predefined amount of target components has accumulated in the transfer channel or the collection channel, the signal from the sensor to the controller can cause the controller to change (e.g. increase) the flow in the collection channel, or initiate the flushing operation. At the same time the controller can stop the pump 106 and/or operate the valves 103, 107 to stop or reduce the flow of the source fluid through the source channel 224.

As shown in FIGS. 2A, 2B, 2C and 2D, the microfluidic device 102 can include one or more transfer channels 214 (i.e. oriented along the z-direction) connecting the source channels 210 with the collection channels 224. While the transfer channels 214 are shown oriented substantially perpendicular to the source channels 224 and collection channels 210, the transfer channels can be oriented in a range of angles (e.g., 5 to 90 degrees, where 0 degrees corresponds to the direction of flow in the source channels 224, see FIG. 3B) with respect to the source channels 240. The transfer channels 214 can be rectangular in cross-section although other cross-sectional shapes can be used. The number, size, shape, orientation and spacing of the collection fluid channels 210 and the source channels 224, as well as the transfer channels 214 can be varied depending on the desired system performance and efficiency.

In the embodiment where the source fluid is blood, the source channels and the collection channels of the microfluidic device are analogous to the splenic arterioles and venules, respectively; the transfer channels mimic the vascular sinusoids of the spleen where flow is episodic and opsonized particles are retained; and the carrier fluid channels mimic the lymphatic fluids that eventually clear the opsonized particles.

The transfer channels 214 serve to transport magnetic particles attached to target components from the source channels 224 to eventually be flushed out of the microfluidic device 102 via the collection channels 210. The target components bound to the magnetic particles (e.g. paramagnetic or superparamagnetic beads) can be separated from the remaining components of the source fluid flowing in the source channels 224 by applying an external magnetic force that drives the magnetic particles into the transport channels 214.

FIGS. 2B and 2C illustrate one embodiment of the invention where the microfluidic device 102 is partitioned into sections, top portion 202 and bottom portion 204, for example, to facilitate the description or manufacture. Although the microfluidic device 102 can be formed by attaching the two half portions to one another, such as by adhesive or plasma bonding, it is not necessary that the device 102 be formed in this manner. For instance, the microfluidic device 102 can be formed entirely as one polydimethylsiloxane (PDMS) piece having all of the features etched or otherwise incorporated therein, instead of two or more individuals portions attached together.

FIG. 2B shows the top portion 202 which includes an outer surface 216 and an interface surface 218. The interface surface 218 includes a portion of the collection channels 210 formed therein. One or more inlet ports 206 extend from an aperture 206B on the outer surface 216 to an entry 206A of the collection channels 210. Similarly, one or more outlet ports 208 extend from an exit 208A of the collection channels 210 at the interface surface 218 to an aperture 208B on the outer surface 216. Between the inlet port 206 and the outlet port 208, one or more collection channel branches 210 can be arranged in the top portion 202 which allow the collection fluid to travel through the device 102 (FIG. 2A).

FIG. 2C shows the bottom portion 204. The bottom portion 204 can include an outer surface 220 and an interface surface 222, wherein the interface surface 222 comes into contact with interface surface 218 of the top portion 202. The bottom portion 204 includes at least a portion of the collection channels 210 formed in the interface surface 222, whereby the top portion 202 (FIG. 2B) and the bottom portion 204 together form the enclosed collection channels 210 when the top portion 202 and bottom portion 204 are attached together to form the entire microfluidic device 102. Alternatively, the bottom portion 204 can be formed from two sections in a similar fashion as with top portion 202 and bottom portion 204.

As shown in FIG. 2C, the bottom portion 204 includes the one or more source channels 224 which are in communication with inlet port 230 and outlet port 232. The inlet port 230 and the outlet port 232, respectively extend from apertures 230B and 232B in the outer surface 220 to the entry 230A and the exit 232A of the source channels 224.

Figure 3A:
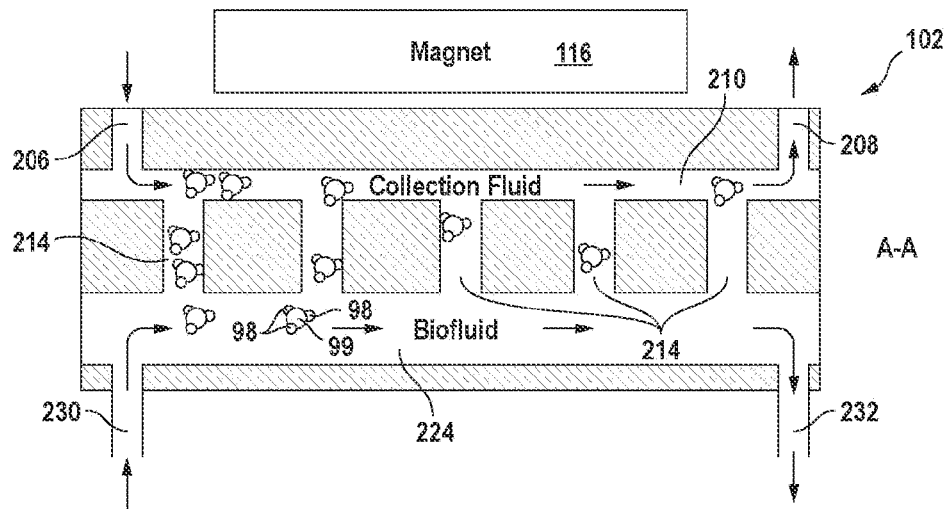
FIGS. 3A and 3B show a cross-sectional view of a fluidic device according to the present invention.

As also shown in FIG. 2C, the bottom portion 102B can include one or more individual, discrete transfer channels 214 in fluid communication with the collection channels 210 and the source channels 224. In the figures, it is shown that the transfer channels 214 are oriented substantially perpendicular to the collection fluid channels 210 and the source channels 224. However, the transfer channels 214 can be oriented at a 5 to 180 degree angle with respect to collection channels 210 relative to the direction of flow, as shown in FIG. 3A. In one embodiment, the transfer channel(s) 214 can be oriented at a 90 to 150 degree angle with respect to the direction of flow in the collection channel(s) 210.

Figure 4A:
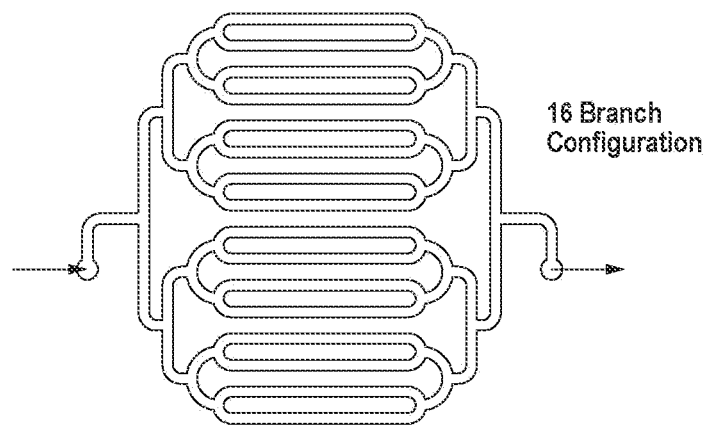
FIGS. 4A and 4B show various branching configurations of fluidic devices according to the present invention.
Figure 4B:
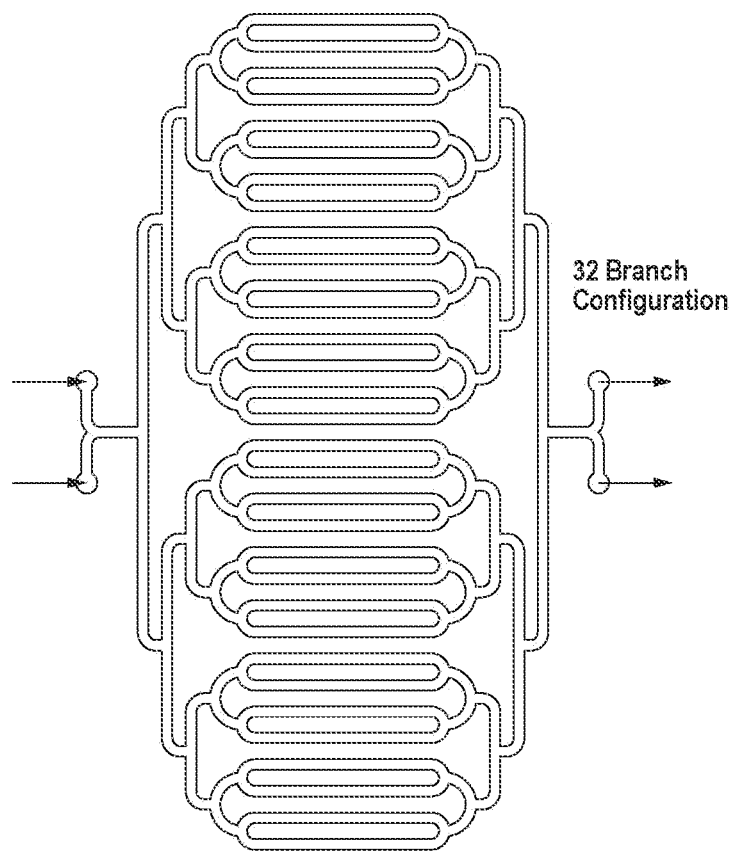

As shown in FIGS. 2A-2D, the collection channels 210 as well as the source channels 224 can branch out into individual branches from their respective inlet ports and the individual branches of the collection channels 210 and the source channels 224 converge to their respective outlet ports. Although four branches are shown in FIGS. 2A-2D, any number of branches, even one branch, can be used. For example, FIG. 4A illustrates 16 branches each of the collection channels and source channels, and FIG. 4B illustrates 32 branches each of collection channels and source channels in accordance with the invention. As one of ordinary skill will appreciate, the number of branches can be selected as a function of the desired performance and efficiency of the system.

In one embodiment according to the invention, the collection channels 210 and the source channels 224 can mirror each other and have the same or similar branched configuration. In addition, each individual branch of the source channels 224 and the corresponding branch of the collection channels 210 can include at least one transfer channel 214 connecting them.

In accordance with the invention, the overall microchannel assembly preferably forms a sealed and enclosed set of channels which allow the fluids to travel between the device without leakage or such. For clarity, this enclosed assembly in hereinafter referred to as the first channel assembly.

It should also be noted that the configurations of one or more of the microchannel assemblies as well as the overall device can have other designs and should not be limited to that shown in the figures. Further, although the channels in the channel assemblies may be shown to have a circular cross section, the channels can have other cross-sectional shapes including, but not limited to square, rectangular, oval, polygonal and the like, or channels that vary in their dimensions and shape along their length as can be created with micromaching technologies.

Figure 2D:
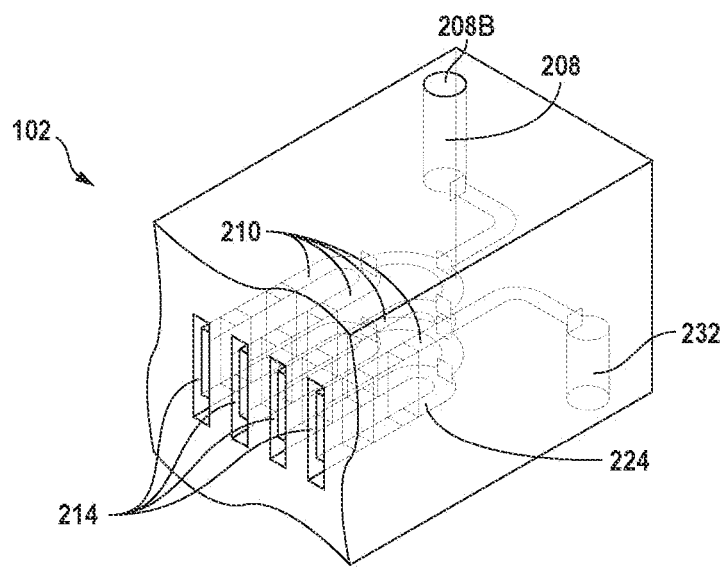

The microfluidic device 102 can be microfabricated by plasma bonding two or more individual layers of micromolded polydimethylsiloxane (PDMS) or other biocompatible materials (e.g., micromachined or laser etched polyimide). As shown in FIGS. 2C and 2D, the bottom portion 204 can be formed to include two distributed networks of microfluidic channels 210 and 224 connected to their respective inlet and outlet ports, although the device can include any number of channels and ports. As shown in FIGS. 2C and 2D, the channels 210 and 224 can be parallel with one another and connected to one another by the transfer channels 214. The top portion 202 shown in FIG. 2B can be formed to include a network of channels 210 on its interface surface 218 in which the channels 210 face toward the channels 210 of the bottom portion 204. The PDMS portions 202, 204 can be aligned, apposed and bonded to form the resulting microfluidic device 102.

FIG. 3A illustrates a cross-sectional view of a microfluidic device in accordance with the present invention. As shown in FIG. 3A, a source fluid, for example a biofluid, such as blood, urine, cerebrospinal fluid, lymph, mucus, tears or sputum enters the source channel 224 via the inlet 230, wherein the biofluid (shown by arrows) passes through the device 102 via the source channel 224 and exits the device 102 via outlet 232.

In accordance with one embodiment, the source fluid can be a biofluid that contains target components 99, such as pathogens, including bacteria and yeast, cancer/tumor cells or a desirable target component such a stem cell, fetal cell, cytokine or antibody. These target components 99 can be mixed with magnetic particles such as paramagnetic or superparamagnetic beads 98 which are conditioned or modified to attach to the predetermined target components 99 prior to entering the microfluidic device 102.

In order to capture the target components 99 from the flowing biofluid, one or more magnetic sources 216, such as Neodymium magnets, can be positioned adjacent to the collection channel 210 of the microfluidic device 102. It should be noted that other types of magnets can be used and are thus not limited to Neodymium. For instance the magnet(s) can be made of Samarium Cobalt, Ferrite, Alnico and the like, or an internal or external electromagnet may be used to generate magnetic field gradients. As shown in FIG. 3A, the magnet 116 is positioned vertically over the transfer channels 214, such that magnetic field gradient applied by the magnet 116 attract the magnetic beads 98 and cause the magnetic beads 98 to move toward the magnet 116. Specifically, the magnetic field gradient from the magnet 116 causes the magnetically bound target components 99 in the source fluid to migrate through the transfer channels 214a into the collection channel 210. These components can be removed and collected when the collection fluid is flushed there through. In some embodiments of the invention, the magnetically bound target components 99 can migrate into and settle in the transfer channels 214 to be drawn into the collection channel 210 by the flushing operation. It should be noted that although the source fluid and the collection fluid are shown flowing in the same direction within the microfluidic device 102, the source fluid and the collection fluid can flow in opposite directions within the microfluidic device 102.

As shown in FIG. 3A, collection fluid enters the collection fluid channel 210 via inlet port 206 and passes through the collection fluid channel 210 toward the outlet port 208. It should be noted that the collection channel 210, and desirably the ports 206 and 208, are filled to capacity with the collection fluid. However, in some embodiments, the collection fluid does not continually flowing through the collection channel 210, and instead is flowed through the collection channel 210 intermittently or on a periodic basis where there are intervals in which the collection fluid flows and intervals in which the collection fluid is stationary or flows at a slower rate. Because the collection fluid is not continuously flowing, but is allowed to become stagnant in the collection channel 210, the magnetically bound target components entering the transfer channels can become retained in these transfer channels 214 for a time without exiting the device.

In accordance with one embodiment of the invention, once the collection fluid begins flowing, changing from the stagnant condition to a flowing condition in the collection channel 210, the magnetically bound target components remaining in the transfer channels 214 can be drawn into the collection channel 210, analogous to the periodic flow of lymph fluid that carries away waste material from the sinuses of the spleen. The flowing collection fluid in the collection channels can have a lower static pressure relative to the transfer channels and cause the magnetic beads and bound target components present in the transfer channels to flow into the collection fluid stream. This predetermined pressure or flow differential can be created when the collection fluid flows through the collection channels 210 during the "flushing" operation, wherein the flushing operation can be controlled to have a desired duration. By controlling the duration of the flushing operation, the amount of source fluid that transfers into the collection channels 210 can also be controlled.

In accordance with one embodiment of the invention, the transfer channel(s) 214 can be oriented substantially perpendicular to the collection channel 210 and the source channel 224. This perpendicular configuration exploits the Bernoulli principle that the collection fluid flowing in the collection channel 210 will have the lower static pressure compared to the fluid in the transfer channel(s) 214 and cause the magnetic beads and bound target components in the transfer channel(s) 214 to be drawn into the collection fluid.

Figure 3B:
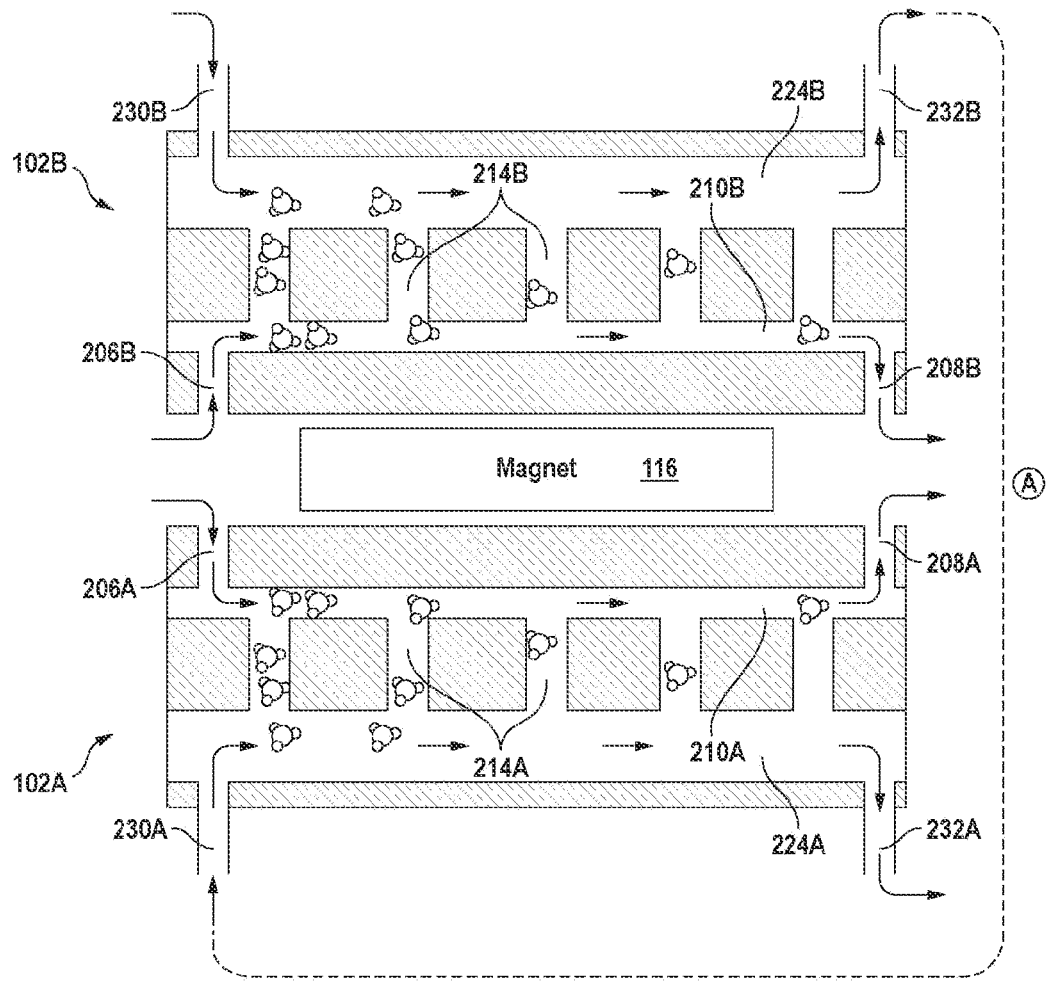

FIG. 3B illustrates a multiplexed system in accordance with an aspect of the present disclosure. As shown in FIG. 3B, a first microfluidic device 102A and a second microfluidic device 102B are positioned adjacent to one another and separated by one or more magnetic sources 240. It should be noted that although only two microfluidic devices 102A, 102B are shown, more than two microfluidic devices may be utilized. In the multiplexed system shown in FIG. 3B, the microfluidic devices 102A, 102B may be connected together in series to maximize throughput flow of the biofluid sample. In particular, the biofluid sample enters the microfluidic device 102B via inlet 226B and passes through the biofluid channel(s) 224B. A magnet force from the magnetic source 240 attracts the paramagnetic or superparamagnetic beads 98 attached to target components 99 toward the magnetic source 116 and cause the paramagnetic beads 98 and bound target components 99 to move from the source channel(s) 224B into the transfer channels 214B.

Upon exiting out of microfluidic device 102B via the outlet 232B, the system may be configured to direct the source fluid into the microfluidic device 102A via the inlet 224A (as shown by dashed line A in FIG. 3B). As with device 102B, the magnet field gradient from the magnetic source 116 attracts the paramagnetic beads 98 attached to target components 99 toward the magnetic source 116 causing the paramagnetic beads 98 and target components 99 to move from the source channel(s) 224A into the transfer channel(s) 214A. The source fluid then exits from the microfluidic device 102A via outlet 228A. In this sandwiched configuration, the devices can then be connected in series or in parallel to maximize the cleansing efficiency or throughput flow rate, respectively.

Figure 5A:
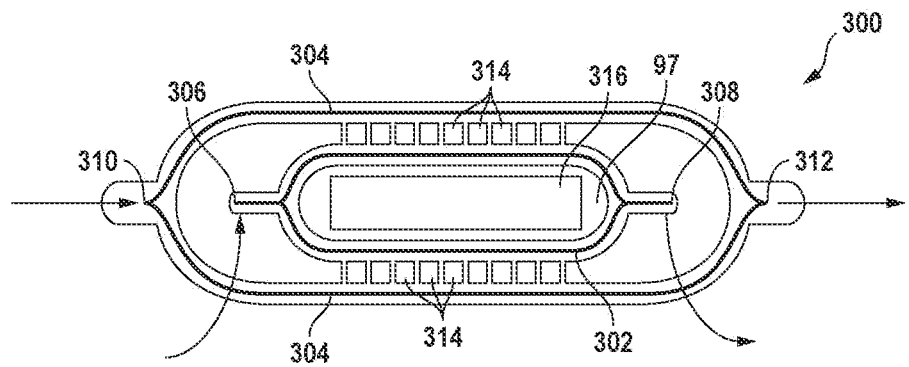
FIGS. 5A and 5B show alternative configurations of fluidic devices according to the present invention.

FIG. 5A illustrates a schematic of a microfluidic device in accordance with an aspect of the present disclosure. As opposed to the microfluidic device shown in FIG. 2A in which the source channel(s) 224 and the collection channel(s) 210 are vertically separated by the transfer channel(s) 214, the collection channel(s) 302 and the source channel(s) 304 in the microfluidic device 300 can be horizontally co-planar and concentric with respect to a center aperture 301.

In accordance with the invention, the device 300 includes a collection channel(s) 302 located around center aperture 301 in which the collection fluid enters the collection channel(s) 302 via an inlet port 306 and exits the collection channel(s) 302 via the outlet port 308. The device 300 can also include a source channel(s) 304 concentric with the collection channel(s) 302, wherein the source fluid enters the channel(s) 304 via an inlet port 310 and exits the channel(s) 304 through the outlet port 312.

One or more transfer channels 314 can be positioned between the inner collection channel(s) 302 and the outer source channel(s) 304, wherein magnetically bound target components migrate from the source channel(s) 304 into the transfer channels 314 in response to an applied magnetic field gradient provided by magnet 316. Although the transfer channels 314 are shown along the portions of the channels 302 and 304 that are parallel to each other (i.e. along the sides), the transfer channels 314 can be included along other areas, such as near the inlet ports and/or outlet ports of the channels 302, 304. In addition, the transfer channels 314, while show perpendicular to the collection channel(s) 302 and the source channel(s) 304, one or more of the transfer channels 314 can be arranged at an angle with respect to either the source channel(s) 304, the collection channel(s) 302 or both.

Figure 5B:
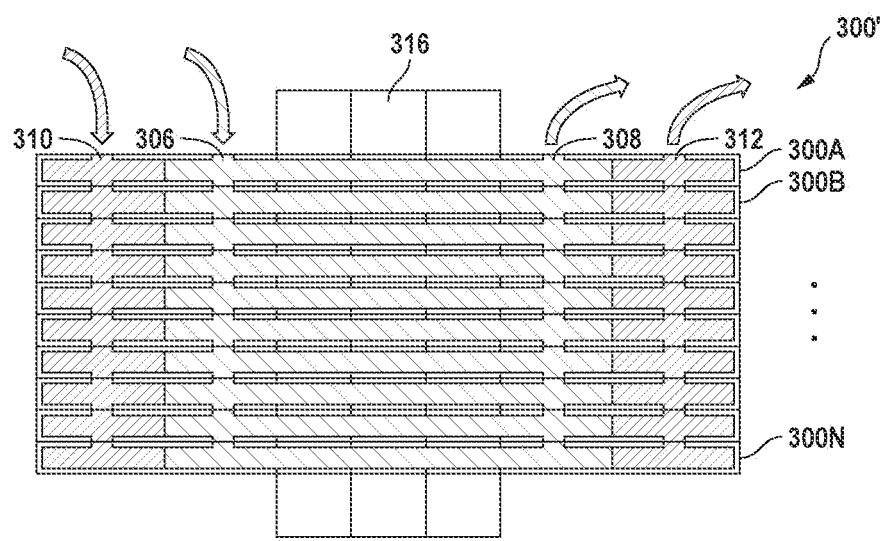

As shown in FIGS. 5A and 5B, the channels 302, 304 and 314 are substantially coplanar such that the entire device 300 maintains a thin cross sectional profile. Positioned within the center aperture 301 is one or more magnets 316 which apply magnetic field gradients upon the magnetic particles traveling on the outer source channel(s) 304. The magnetic field gradients cause magnetic beads with the attached target components to move from the outer source fluid channel(s) 304 toward the inner collection channel(s) 302 via the transfer channels 314. Upon a flushing operation, collection fluid is flowed through the inner collection channel(s) 302 and exits through port 308. As the collection fluid is flowed through channel(s) 302, the magnetically bound target components flow from the transfer channels 314 into the collection channel(s) 302 and then eventually flow out of the device 300 via port 308.

FIG. 5B illustrates a side view of a series of microfluidic devices 300A, 300B, through $300_N$ arranged in a multiplexed system in accordance with an aspect of the present disclosure. As shown in FIG. 5B, several microfluidic devices 300A, 300B and so on are vertically disposed on one another and are positioned such that their center apertures 301 are aligned to receive one or more magnets 316 therein. Although the details are not shown in FIG. 5B, the microfluidic devices may be connected to one another in a series fashion, parallel fashion and a combination of series/parallel connections. The stacking ability of the embodiments shown in FIGS. 5A and 5B allow several devices to be connected in a multiplexed manner while limiting the amount of space used by the system. Further, the aligned centers of the devices allow one magnet to produce a relatively uniform magnetic field gradient to all of the devices at one time.

The microfluidic devices described in FIGS. 2A-2D as well as FIGS. 5A and 5C can include one or more optical or impedance microelectronic sensors integrated therein which detect target component or pathogen buildup. The microfluidic devices can incorporate a feedback loop in which sensors communicate with a controller and/or one or more pumps to automatically control the flow (e.g. start/stop duration, flow rate, and the like) of the collection fluid. In addition, one or more magnetic bead traps, external to the microfluidic device, can be used in the system in FIG. 1 to remove any remaining particles that are not cleared by other mechanisms before the source fluid is returned to the source or input to the source fluid collector. The microfluidic device can include one or more valves at the inlets and/or outlets of the collection channels and/or source fluid channels. The microfluidic device can include one or more valves at the transfer channels to control the flow of the magnetically bound target components entering or exiting the transfer channels.

Figure 6:
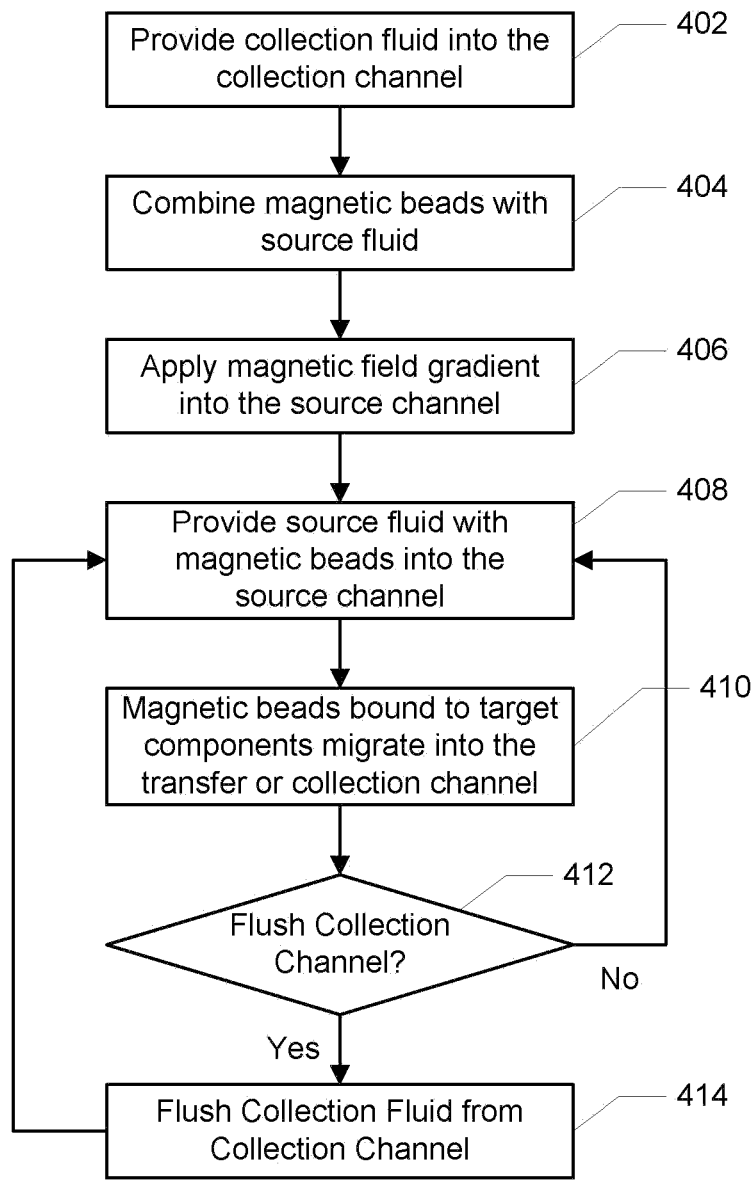
FIG. 6 shows a flow chart of a method for using a fluidic device according to the invention.

FIG. 6 shows a flow chart of a method for processing a fluid to remove target components bound to magnetic beads using a fluid processing device according an embodiment of the present invention. In accordance with the invention at 402, the collection fluid can be pumped into the collection channel and fill some or all of the transfer channels and the source channels. At 404, the source fluid can be combined, such as by mixing, with the magnetic beads. The magnetic bead can be include an affinity coating that enables target components in the source fluid to bind to the magnetic beads. At 406, the magnetic field gradient can be applied to the source channel, such as by applying power to an electromagnet or positioning permanent magnets at a predefined location with respect to the source channel. At 408, the source fluid is pumped into and through the source channel, exposing the magnetic beads (and any target components bound thereto) to the magnet field gradient. At 410, the magnetic bead and target components migrate through the transfer channels to the collection channels. At 412, the system checks to determine whether a defined amount of magnetic beads have accumulated in the collection channel and the collection channel needs to be flushed. This can be after a predefined volume of source fluid flow or after a predefined period of time or based on a signal from a sensor, collection fluid can be allowed to flow into the collection channel, flushing the collection channel and magnetic beads out of the collection channel. During the flushing process, the source fluid flow can be reduced or stopped for the duration of the flushing process. If enough magnetic beads have not accumulated in the collection channel, the process returns to 408 and the source fluid continues to flow into the source channel.

Microfluidic Devices, Systems and Methods

In one or more embodiments of the invention, a microfluidic biomimetic blood cleansing device is provided. The device contains one or more source channels where one or more fluids or biofluids (e.g. blood) flow therethrough. The device can also include one or more collection channels where one or more collection fluids (e.g. sterile isotonic saline) flows at predetermined start-and-stop intervals. The device can also include one or more transfer channels provide fluid communication between the source channels and the collection channels. A permanent magnet or an electromagnet can be used to generate magnetic field gradients that are directed toward the source channels, whereby the strong magnetic field gradients direct magnetically bound target components, such as cells, molecules, and/or pathogens, to migrate from the source fluid and into the transfer channels and optionally, into the collection channels. Examples of electromagnets as well as associated plates for shaping and/or concentrating the magnet field gradient are disclosed published US Patent Application No. 2009-0078614. A periodic flow of the collection fluid through the collection channels can cause the magnetically bound target components in the transfer channels to flow into the collection fluid, whereby the target cells can then be removed and collected by flushing them from the device. Multiplexing can be achieved by increasing the number of channels within each device, and by stacking up multiple devices in parallel and/or serial configurations.

The designs described herein have several advantages when compared to previous magnetic separation flow cells. A separate magnetic field gradient concentrator layer can be employed with surface ridges that run directly above the entire length of each channel to shape and/or concentrate the magnetic field gradient applied to the source channel. Since this magnetic field concentrator is not placed within the PDMS layers of the device, multiple channels can be densely arrayed within a single polymeric device to increase throughput. In some embodiments of the invention, further multiplexing can be achieved by stacking multiple devices vertically, interposed with multiple magnetic field gradient concentrators that are placed between each PDMS layer inside a single electromagnet housing. In an example, the magnetic source can be an electromagnet constructed from a 1500 turn, 47 solenoid and a C-shaped steel core, although other magnet designs can be used. The magnetic field concentrator, also machined from high magnetic permeability steel, can have four individual ridges (1×1×20 mm; w×h×l), spaced 3 mm apart, and be attached to the top side of the magnet. The total air gap between the top surface of the ridges and the opposing face of the magnet is 5.7 mm. The electromagnetic field strength of the concentrator can be measured using a Teslameter (F.W. Bell 5080) and field gradient can be quantified by measuring the change in the field strength at a distance of 0.25 mm normal to the surface of a ridge.

In accordance with the invention and described herein are micromagnetic microfluidic biomimetic devices, methods of use, and systems for therapeutic applications and for high throughput processes (1000 L/h), such as extracorporeal blood cleansing. Such devices comprise an array of vertically aligned channels that utilizes a separate magnetic field concentrator placed external to the device. The advantage of such designs is that it allows channels to be densely arrayed within each device. Additionally, multiple such devices can be stacked with interposed magnetic field gradient concentrators, which ensures application of similar magnetic pulling forces across multiple interposed microfluidic systems, to achieve high throughput processing required for therapeutic applications, such as extracorporeal blood cleansing. In accordance with the invention, the source fluid can flow through a single source channel at a rate ranging from 1 mL/hr to 1000 L/hr depending on the fluid and device characteristics. In addition, the collection fluid can flow through a single collection channel at a rate ranging from 1 mL/hr to 1000 L/hr depending on the fluid and device characteristics.

In one or more embodiments of the aspects described herein, a multiplexed device of the present invention was capable of over 80% and as high as 95% cleansing of living fungal pathogens from a whole blood without inducing blood coagulation or causing significant loss of other blood cellular or molecular components. In some such embodiments, whole blood can flow at a rate of 20 mL/h, which is 1,000 times faster than previously achieved with other microfluidic-micromagnetic separator devices that rely on two adjacent flowing fluids in a single microfluidic channel(s) such as disclosed in US 2009-0078614 and US 2009-0220932. Our results clearly demonstrate that the novel multiplexed microfluidic-micromagnetic cell separation designs described herein provide much higher volume throughput while maintaining cell separation efficiencies, and thus, confirm their value for clinical applications such as blood cleansing.

In other embodiments, semi-batch mixing processes are provided that allow longer bead-pathogen incubation periods while maintaining continuous blood flow. Such processes also enable integration into conventional continuous venovenous hemafiltration units, which use hemaconcentrators, blood warmers and oxygenation technologies. In some further embodiments, additional safety features such as ultra-high-efficiency magnetic traps are also be added to the devices described herein to remove all remaining magnetic particles before the cleansed biofluid is returned to the biological system, such as a septic patient.

Innovations of the present design over previous designs for microfluidic-micromagnetic cell separators include that it requires neither (a) a second continually flowing stream of collection fluid (e.g., saline), nor (b) maintenance of a stable boundary between two laminar flow streams (which are central elements in the microfluidic devices described previously in US 2009-0078614 and US 2009-0220932) to remove particles. Thus, the present system is improved by its simplicity and robustness; blood also cannot be lost or diluted due an imbalance of hydrodynamics between blood and saline solutions. In this biomimetic design, the middle layer emulates the sinus of the spleen where blood flow rate is relatively slow and episodic, and opsonized pathogens are retained. Saline in the top layer is then used to periodically flush out the "sinus", and this emulates the percolating flow of waste and lymph fluids through the lymphoid follicles.

In conclusion, this system exhibits simplicity of design and fabrication, very high flow throughput, higher separation efficiency, and minimal blood alteration (e.g., clots, loss, dilution). This simple design also obviates the need for complex control of two fluids and maintenance of a stable border between adjacent laminar flow streams, and simplifies multiplexing. It will likely be less expensive and simpler to manufacture and assemble, and exhibit a similar or enhanced ability to be integrated into existing blood filtration biomedical devices such as those used for continuous renal replacement therapy (CRRT), extracorporeal membrane oxygenation (ECMO), and continuous veno-venous hemofiltration (CVVH).

Methods for filtering a biological fluid utilizing a biomimetic microfluidic device are also provided. In one aspect, the method comprises first passing a biological fluid through a first microfluidic channel within a biomimetic microfluidic device, where the biological fluid contains magnetic particles attached to biological target component cells or particles; placing a collection fluid in a second microfluidic channel within the biomimetic microfluidic device, such that the second microfluidic channel is in communication with the first microfluidic channel via one or more discrete transfer channels; and applying a magnetic field gradient to the biological fluid, such that the magnetic field gradient causes the magnetic particles and the target component cells or particles to migrate from the first microfluidic channel into the second microfluidic channel via the at least one discrete transfer channel.

In one or more embodiments of this aspect, the method further comprises initiating flow for a selected amount of time, where the magnetic particles in the collection fluid are removed from the biomimetic microfluidic device.

In other embodiments of this aspect, the method further comprises passing at least a portion of the removed biological fluid back into the first microfluidic channel.

In one or more embodiments of this aspect, the method further comprises collecting at least a portion of the collection fluid and target components from the second microfluidic channel.

In other embodiments of this aspect, the method further comprises adding the magnetic particles into the biological fluid prior to the biological fluid being supplied to the first microfluidic channel.

In further embodiments of this aspect, the passing of the collection fluid further comprises intermittently passing the collection fluid through the second microfluidic channel at irregular or periodic intervals.

In one or more embodiments of this aspect, the biological fluid is selected from one or more in a group comprising blood, cord blood, serum, plasma, urine, liquefied stool sample, cerebrospinal fluid, amniotic fluid, lymph, mucus, tears, tracheal aspirate, sputum, saline, a buffer, a physiological salt solution or a cell culture medium. In one or more embodiments of this aspect, the collection fluid is isotonic saline. In one or more embodiments of this aspect, the target cells are one or more from a group comprising a pathogen, a stem cell, a cancer cell, a fetal cell, a blood cell or an immune cell. In one or more embodiments of this aspect, the target components are one or more from a group comprising a cytokine, a hormone, an antibody, a blood protein, or a molecular or chemical toxin.

In other embodiments of this aspect, the magnetic particles are coated with a ligand configured to bind the magnetic particles to a biological target cell, molecule or particulate. The ligand can be for example, an antibody or a ligand binds to a surface molecule or receptor that is expressed by the biological target cell.

Also described herein are systems for isolating target cells, molecules or particulates. In one aspect a system for isolating target cells, molecules or particulates is provided, comprising a biomimetic microfluidic device or a plurality of devices, where each biomimetic microfluidic device includes a first microfluidic channel and a second microfluidic channel and at least one discrete internal transfer channel in communication with the first and second microfluidic channels; a fluid source configured to supply a biological fluid containing magnetic particles bound to target cells, molecules or particulates to at least one of the biomimetic microfluidic devices, where the biological fluid passes through the first microfluidic channel in the at least one biomimetic microfluidic device; a collection fluid source configured to supply a collection fluid to the at least one biomimetic microfluidic device, where the collection fluid passes through the second microfluidic channel at selected periods of time; and at least one magnet configured to apply a magnetic field gradient to biological fluid flowing in at least one biomimetic microfluidic device, where the magnetic particles and the target cells, molecules or particulates in the biological fluid migrate from the biological fluid into the collection fluid via at least one transfer channel in response to the magnetic field gradient.

In one or more embodiments of the aspect, two or more of the plurality of biomimetic microfluidic devices are connected to another in parallel. In other embodiments of the aspect, two or more of the plurality of biomimetic microfluidic devices are connected to another in serial.

In one or more embodiments of the aspect the collection fluid is intermittently passed through the second microfluidic channel at periodic or aperiodic intervals.

In one or more embodiments of this aspect, the biological fluid is selected from one or more in a group comprising blood, cord blood, serum, plasma, urine, liquefied stool sample, cerebrospinal fluid, amniotic fluid, lymph, mucus, tears, tracheal aspirate, sputum, saline, a buffer, a physiological salt solution or a cell culture medium. In one or more embodiments, the collection fluid is isotonic saline.

In one or more embodiments of this aspect, the target cells are one or more from a group comprising a pathogen, a stem cell, a cancer cell, a progenitor cell, a fetal cell, a blood cell or an immune cell. The pathogen can be selected from one or more in a group comprising a viral particle, a bacterial cell, a fungal cell or a protozoan cell.

In one or more embodiments of this aspect, the at least one transfer channel is oriented perpendicular to the orientation of the first and second microfluidic channels.

In one or more embodiments of this aspect, the magnetic particles are coated with a ligand configured to bind the magnetic particles to the target cells, molecules or particulates.

In one aspect, a method of detecting a biological target in a biological fluid the method comprising adding magnetic particles targeted to attach to a target cell, molecule or particulate into the biological fluid; and passing the biological fluid through a first microfluidic channel within a biomimetic microfluidic device; placing a collection fluid in a second microfluidic channel within the biomimetic microfluidic device, the second microfluidic channel in communication with the first microfluidic channel via at least one discrete transfer channel; applying a magnetic field gradient to the biological fluid flowing through the device, wherein the magnetic field gradient causes the magnetic particles to migrate from the first microfluidic channel into the second microfluidic channel via at least one discrete transfer channel; collecting at least a portion of the collection fluid having magnetic particles in it from the second microfluidic channel; and detecting whether any of the target cell, molecule or particulates bound to the magnetic particles contain the biological target.

In one aspect the method further comprises separating the magnetic particles from the collection fluid prior to detecting whether any of the magnetic particles contain the biological target.

The biological target can be selected from one or more in a group comprising a pathogen, a cancer cell, a stem cell, a progenitor cell, a fetal cell, a blood cell or an immune cell.

The pathogen can be selected from one or more in a group comprising a viral particle, a bacterial cell, a fungal cell, or a protozoan cell.

In one aspect, one can further quantify the amount of biological target attached to the magnetic particles.

As used herein the term "comprising" or "comprises" is used in reference to compositions, methods, and respective component(s) thereof, that are essential, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

The devices described herein can be fabricated from a biocompatible material. As used herein, the term "biocompatible material" refers to any polymeric material that does not deteriorate appreciably and does not induce a significant immune response or deleterious tissue reaction, e.g., toxic reaction or significant irritation, over time when implanted into or placed adjacent to the biological tissue of a subject, or induce blood clotting or coagulation when it comes in contact with blood. Suitable biocompatible materials include derivatives and copolymers of a polyimides, poly(ethylene glycol), polyvinyl alcohol, polyethyleneimine, and polyvinylamine, polyacrylates, polyamides, polyesters, polycarbonates, and polystyrenes.

In some embodiments, the device is fabricated from a material selected from the group consisting of polydimethylsiloxane, polyimide, polyethylene terephthalate, polymethylmethacrylate, polyurethane, polyvinylchloride, polystyrene polysulfone, polycarbonate, polymethylpentene, polypropylene, a polyvinylidine fluoride, polysilicon, polytetrafluoroethylene, polysulfone, acrylonitrile butadiene styrene, polyacrylonitrile, polybutadiene, poly(butylene terephthalate), poly(ether sulfone), poly(ether ether ketones), poly(ethylene glycol), styrene-acrylonitrile resin, poly(trimethylene terephthalate), polyvinyl butyral, polyvinylidenedifluoride, poly(vinyl pyrrolidone), and any combination thereof.

In some embodiments, the device can be fabricated from materials that are compatible with the fluids used in the system. While the plastics described herein can be used with may fluids, some materials may break down when highly acidic or alkaline fluids are used and it is recognized that the removal of the target component from the source fluid can change the composition and characteristics of the source fluid. In these embodiments, other materials such as stainless steels, titanium, platinum, alloys, ceramics and glasses can be used. In addition, the channel(s) can be coated or treated to resist degradation or facilitate flow and operation. In some embodiments, it can be desirable to use different materials in the source channel(s), the transfer channel(s) and the collection channel(s).

Magnetic Particles

The magnetic particles or beads can be of any shape, including but not limited to spherical, rod, elliptical, cylindrical, disc, and the like. In some embodiments, magnetic particles having a true spherical shape and defined surface chemistry are used to minimize chemical agglutination and non-specific binding. As used herein, the term "magnetic particle" refers to a nano- or micro-scale particle that is attracted or repelled by a magnetic field gradient or has a non-zero magnetic susceptibility. The term "magnetic particle" also includes magnetic particles that have been conjugated with affinity molecules. The magnetic particles can be paramagnetic or super-paramagnetic particles. In some embodiments, the magnetic particles are superparamagnetic. Magnetic particles are also referred to as beads herein.

In some embodiments, magnetic particles having a polymer shell are used to protect the target component from exposure to iron. For example, polymer coated magnetic particles can be used to protect target cells from exposure to iron. In some embodiments, the magnetic particles or beads can be selected to be compatible with the fluids being used, so as not to cause undesirable changes to the source fluid. For example, for biofluids, the magnetic particles can made from well know biocompatible materials.

The magnetic particles can range in size from 1 nm to 1 mm. Preferably magnetic particles are about 250 nm to about 250 µm in size. In some embodiments, magnetic particle is 0.1 µm to 50 µm in size. In some embodiments, magnetic particle is 0.1 µm to 10 µm in size. In some embodiments, the magnetic particle is a magnetic nano-particle or magnetic microparticle. Magnetic nanoparticles are a class of nanoparticle which can be manipulated using magnetic field. Such particles commonly consist of magnetic elements such as iron, nickel and cobalt and their chemical compounds. Magnetic nano-particles are well known and methods for their preparation have been described in the are art, for example in U.S. Pat. Nos. 6,878,445; 5,543,158; 5,578,325; 6,676,729; 6,045,925 and 7,462,446, and U.S. Pat. Pub. Nos.: 2005/0025971; 2005/0200438; 2005/0201941; 2005/0271745; 2006/0228551; 2006/0233712; 2007/01666232 and 2007/0264199, contents of all of which are herein incorporated by reference in their entirety.

Magnetic particles are easily and widely available commercially, with or without functional groups capable of binding to affinity molecules. Suitable superparamagnetic particles are commercially available such as from Dynal Inc. of Lake Success, N.Y.; PerSeptive Diagnostics, Inc. of Cambridge, Mass.; Invitrogen Corp. of Carlsbad, Calif.; Cortex Biochem Inc. of San Leandro, Calif.; and Bangs Laboratories of Fishers, Ind. In some embodiments, magnetic particles are Dynal Magnetic beads such as MyOne Dynabeads.

Magnetic Particle—Target Component Binding

The degree of magnetic particle binding to a target component is such that the bound target component will move when a magnetic field is applied. It is to be understood that binding of magnetic particle with the target component is mediated through affinity molecules, i.e., the affinity molecule on the surface of the magnetic particle that binds to the target component. Binding of magnetic particles to target components can be determined using methods or assays known to one of skill in the art, such as ligand binding kinetic assays and saturation assays. For example, binding kinetics of a target component and the magnetic particle can be examined under batch conditions to optimize the degree of binding. In another example, the amount of magnetic particles needed to bind a target component can be ascertained by varying the ratio of magnetic particles to target component under batch conditions. Without wishing to be bound by theory, the binding efficiency can follow any kinetic relationship, such as a first-order relationship. In some embodiments, binding efficiency follows a Langmuir adsorption model.

The separation efficiency of a microfluidic device described herein can be determined using methods known in the art and easily adaptable for microfluidic devices. For example, magnetic particle conjugated with an affinity molecule and the target component are pre-incubated in the appropriate medium to allow maximum binding before resuspending in a source fluid such as a biological fluid. The effects of varying electromagnet current on separation efficiency can be analyzed using, for example, target component-magnetic particle complexes suspended in PBS. To test how the viscosity of the collection fluid affected its hydrodynamic interaction with a biological fluid, such as blood, medical grade dextran (40 kDa, Sigma) can be used to vary the viscosity. For example, dextran can be dissolved in PBS at 5, 10 and 20% to produce solutions with viscosities of 2, 3, 11 centipoise at room temperature. Samples can be collected from bottom-inlet, top-outlet, and bottom-outlet channels and analyzed by flow cytometry to assess the separation efficiency of magnetic particles and particle bound target components. Efficiency can be calculated as: Efficiency=$1-X_{bottom-out}/X_{bottom-in}$. Source fluid loss can be quantified using an appropriate marker in the source fluid. For example, blood loss can be quantified by measuring the OD600 of red blood cells (Loss=$OD_{top-out}/OD_{bottom-out}$).

The optimal time for binding of magnetic particles to target component can vary depending on the particulars of the device or methods being employed. The optimal mixing and/or incubation time for binding of magnetic particles to a target component can be determined using kinetic assays well known to one of skill in the art. For example, kinetic assays can be performed under conditions that mimic the particulars of the device or methods to be employed, such as volumes, concentrations, how and where the mixing is to be performed, and the like. The rate of binding of magnetic particles to target components can be increased by carrying out mixing within separate microfluidic mixing channels.

Binding/Affinity Molecules

The surfaces of the magnetic particles are functionalized to include binding molecules that bind selectively with the target component. These binding molecules are also referred to as affinity molecules herein. The binding molecule can be bound covalently or non-covalently (e.g. adsorption of molecule onto surface of the particle) to each magnetic particle. The binding molecule can be selected such that it can bind to any part of the target component that is accessible. For example, the binding molecule can be selected to bind to any antigen of a pathogen that is accessible on the surface, e.g., a surface antigen.

As used herein, the term "binding molecule" or "affinity molecule" refers to any molecule that is capable of specifically binding a target component. Representative examples of affinity molecules include, but are not limited to, antibodies, antigens, lectins, proteins, peptides, nucleic acids (DNA, RNA, PNA and nucleic acids that are mixtures thereof or that include nucleotide derivatives or analogs); receptor molecules, such as the insulin receptor; ligands for receptors (e.g., insulin for the insulin receptor); and biological, chemical or other molecules that have affinity for another molecule, such as biotin and avidin. The binding molecules need not comprise an entire naturally occurring molecule but may consist of only a portion, fragment or subunit of a naturally or non-naturally occurring molecule, as for example the Fab fragment of an antibody. The binding molecule may further comprise a marker that can be detected.

Nucleic acid based binding molecules include aptamers. As used herein, the term "aptamer" means a single-stranded, partially single-stranded, partially double-stranded or double-stranded nucleotide sequence capable of specifically recognizing a selected non-oligonucleotide molecule or group of molecules by a mechanism other than Watson-Crick base pairing or triplex formation. Aptamers can include, without limitation, defined sequence segments and sequences comprising nucleotides, ribonucleotides, deoxyribonucleotides, nucleotide analogs, modified nucleotides and nucleotides comprising backbone modifications, branchpoints and nonnucleotide residues, groups or bridges. Methods for selecting aptamers for binding to a molecule are widely known in the art and easily accessible to one of ordinary skill in the art.

In some embodiments of the aspects described herein, the binding molecules specific are polyclonal and/or monoclonal antibodies and antigen-binding derivatives or fragments thereof. Well-known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art. Accordingly, as used herein, the term "antibody" refers to an intact immunoglobulin or to a monoclonal or polyclonal antigen-binding fragment with the Fc (crystallizable fragment) region or FcRn binding fragment of the Fc region. Antigen-binding fragments may be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms Fab, Fc, pFc', F(ab')2 and Fv are employed with standard immunological meanings [Klein, Immunology (John Wiley, New York, N.Y., 1982); Clark, W. R. (1986) The Experimental Foundations of Modern Immunology (Wiley & Sons, Inc., New York); Roitt, I. (1991) Essential Immunology, 7th Ed., (Blackwell Scientific Publications, Oxford)]. Antibodies or antigen-binding fragments specific for various antigens are available commercially from vendors such as R&D Systems, BD Biosciences, e-Biosciences and Miltenyi, or can be raised against these cell-surface markers by methods known to those skilled in the art.

In some embodiments, the binding molecule binds with a cell-surface marker or cell-surface molecule. In some further embodiments, the binding molecule binds with a cell-surface marker but does not cause initiation of downstream signaling event mediated by that cell-surface marker. Binding molecules specific for cell-surface molecules include, but are not limited to, antibodies or fragments thereof, natural or recombinant ligands, small molecules, nucleic acids and analogues thereof, intrabodies, aptamers, lectins, and other proteins or peptides.

As used herein, a "cell-surface marker" refers to any molecule that is present on the outer surface of a cell. Some molecules that are normally not found on the cell-surface can be engineered by recombinant techniques to be expressed on the surface of a cell. Many naturally occurring cell-surface markers present on mammalian cells are termed "CD" or "cluster of differentiation" molecules. Cell-surface markers often provide antigenic determinants to which antibodies can bind to.

Accordingly, as defined herein, a "binding molecule specific for a cell-surface marker" refers to any molecule that can selectively react with or bind to that cell-surface marker, but has little or no detectable reactivity to another cell-surface marker or antigen. Without wishing to be bound by theory, affinity molecules specific for cell-surface markers generally recognize unique structural features of the markers. In some embodiments of the aspects described herein, the preferred affinity molecules specific for cell-surface markers are polyclonal and/or monoclonal antibodies and antigen-binding derivatives or fragments thereof.

The binding molecule can be conjugated to the magnetic particle using any of a variety of methods known to those of skill in the art. The affinity molecule can be coupled or conjugated to the magnetic particles covalently or non-covalently. The covalent linkage between the affinity molecule and the magnetic particle can be mediated by a linker. The non-covalent linkage between the affinity molecule and the magnetic particle can be based on ionic interactions, van der Waals interactions, dipole-dipole interactions, hydrogen bonds, electrostatic interactions, and/or shape recognition interactions.

As used herein, the term "linker" means an organic moiety that connects two parts of a compound. Linkers typically comprise a direct bond or an atom such as oxygen or sulfur, a unit such as NH, C(O), C(O)NH, SO, $SO_2$, $SO_2$NH or a chain of atoms, such as substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{12}$ aryl, substituted or unsubstituted $C_5$-$C_{12}$ heteroaryl, substituted or unsubstituted $C_5$-$C_{12}$ heterocyclyl, substituted or unsubstituted $C_3$-$C_{12}$ cycloalkyl, where one or more methylenes can be interrupted or terminated by O, S, S(O), $SO_2$, NH, C(O).

In some embodiments, the binding molecule is coupled to the magnetic particle by use of an affinity binding pair. The term "affinity binding pair" or "binding pair" refers to first and second molecules that specifically bind to each other. One member of the binding pair is conjugated with the magnetic particle while the second member is conjugated with the affinity molecule. As used herein, the term "specific binding" refers to binding of the first member of the binding pair to the second member of the binding pair with greater affinity and specificity than to other molecules.

Exemplary binding pairs include any haptenic or antigenic compound in combination with a corresponding antibody or binding portion or fragment thereof (e.g., digoxigenin and anti-digoxigenin; mouse immunoglobulin and goat anti-mouse immunoglobulin) and nonimmunological binding pairs (e.g., biotin-avidin, biotin-streptavidin, hormone [e.g., thyroxine and cortisol-hormone binding protein, receptor-receptor agonist, receptor-receptor antagonist (e.g., acetylcholine receptor-acetylcholine or an analog thereof), IgG-protein A, lectin-carbohydrate, enzyme-enzyme cofactor, enzyme-enzyme inhibitor, and complementary oligonucleotide pairs capable of forming nucleic acid duplexes), and the like. The binding pair can also include a first molecule which is negatively charged and a second molecule which is positively charged.

In some cases, the target component comprises one member of an affinity binding pair. In such cases, the second member of the binding pair can be conjugated to a magnetic particle as an affinity molecule.

In some embodiments, the target component is first conjugated to one member of an affinity binding pair, and the second member of the affinity binding pair is conjugated to the magnetic particle.

In some embodiments, the magnetic particle is functionalized with two or more different affinity molecules. The two or more different affinity molecules can target the same target component or different target components. For example, a magnetic particle can be functionalized with antibodies and lectins to simultaneously target multiple surface antigens or cell-surface markers. In another example, a magnetic particle can be functionalized with antibodies that target surface antigens or cell-surface markers on different cells, or with lectins, such as mannose-binding lectin, that recognizes surface markers on a wide variety of pathogens.

In some embodiments, the binding/affinity molecule is a ligand that binds to a receptor on the surface of that target cell. Such a ligand can be a naturally occurring molecule, a fragment thereof or a synthetic molecule or fragment thereof. In some embodiments, the ligand is non-natural molecule selected for binding with a target cell. High throughput methods for selecting non-natural cell binding ligands are known in the art and easily available to one of skill in the art. See for example, Anderson, et al., Biomaterial microarrays: rapid, microscale screening of polymer-cell interaction. *Biomaterials* (2005) 26:4892-4897; Anderson, et al., Nanoliter-scale synthesis of arrayed biomaterials and application to human embryonic stem cells. *Nature Biotechnology* (2004) 22:863-866; Orner, et al., Arrays for the combinatorial exploration of cell adhesion. *Journal of the American Chemical Society* (2004) 126:10808-10809; Falsey, et al., Peptide and small molecule microarray for high throughput cell adhesion and functional assays. *Bioconjugate Chemistry* (2001) 12:346-353; Liu, et al., *Biomacromolecules* (2001) 2(2): 362-368; and Taurniare, et al., *Chem. Comm.* (2006): 2118-2120.

In some embodiments, the binding molecule and/or the magnetic particles can be conjugated with a label, such as a fluorescent label or a biotin label. When conjugated with a label, the binding molecule and the magnetic particle are referred to as "labeled binding molecule" and "labeled magnetic particles" respectively. In some embodiments, the binding molecule and the magnetic particles are both independently conjugated with a label, such as a fluorescent label or a biotin label. Without wishing to be bound by theory, such labeling allows one to easily track the efficiency and/or effectiveness of methods to selectively bind the target component in a source fluid. For example, a multi-fluorescence labeling can be used to distinguish between free magnetic particles, free target components and magnetic particle-target component complexes.

As used herein, the term "label" refers to a composition capable of producing a detectable signal indicative of the presence of a target. Suitable labels include fluorescent molecules, radioisotopes, nucleotide chromophores, enzymes, substrates, chemiluminescent moieties, magnetic particles, bioluminescent moieties, and the like. As such, a label is any composition detectable by spectroscopic, photochemical, biochemical, immunochemical, electrical, optical or chemical means needed for the methods and devices described herein. For example, binding molecules and/or magnetic particles can also be labeled with a detectable tag, such as c-Myc, HA, VSV-G, HSV, FLAG, V5, or HIS, which can be detected using an antibody specific to the label, for example, an anti-c-Myc antibody.

Exemplary fluorescent labels include, but are not limited to, Hydroxycoumarin, Succinimidyl ester, Aminocoumarin, Succinimidyl ester, Methoxycoumarin, Succinimidyl ester, Cascade Blue, Hydrazide, Pacific Blue, Maleimide, Pacific Orange, Lucifer yellow, NBD, NBD-X, R-Phycoerythrin (PE), a PE-Cy5 conjugate (Cychrome, R670, Tri-Color, Quantum Red), a PE-Cy7 conjugate, Red 613, PE-Texas Red, PerCP, Peridinin chlorphyll protein, TruRed (PerCP-Cy5.5 conjugate), Fluor X, Fluoresceinisothyocyanate (FITC), BODIPY-FL, TRITC, X-Rhodamine (XRITC), Lissamine Rhodamine B, Texas Red, Allophycocyanin (APC), an APC-Cy7 conjugate, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, Alexa Fluor 790, Cy2, Cy3, Cy3B, Cy3.5, Cy5, Cy5.5 or Cy7.

Target Component

As used herein, the term "target component" refers to any molecule, cell or particulate that is to be filtered or separated from a source fluid. Representative examples of target cellular components include, but are not limited to, mammalian cells, viruses, bacteria, fungi, yeast, protozoan, microbes, parasites, and the like. Representative examples of target molecules include, but are not limited to, hormones, cytokines, proteins, peptides, prions, lectins, oligonucleotides, contaminating molecules and particles, molecular and chemical toxins, and the like. The target components also include contaminants found in non-biological fluids, such as pathogens or lead in water or in petroleum products. Parasites include organisms within the phyla Protozoa, Platyhelminthes, Aschelminthes, Acanthocephala, and Arthropoda.

As used herein, the term "molecular toxin" refers to a compound produced by an organism which causes or initiates the development of a noxious, poisonous or deleterious effect in a host presented with the toxin. Such deleterious conditions may include fever, nausea, diarrhea, weight loss, neurologic disorders, renal disorders, hemorrhage, and the like. Toxins include, but are not limited to, bacterial toxins, such as cholera toxin, heat-liable and heat-stable toxins of *E. coli*, toxins A and B of *Clostridium difficile*, aerolysins, hemolysins, and the like; toxins produced by protozoa, such as Giardia; toxins produced by fungi; and the like. Included within this term are exotoxins, i.e., toxins secreted by an organism as an extracellular product, and enterotoxins, i.e., toxins present in the gut of an organism.

In some embodiments, the target component is a bioparticle/pathogen selected from the group consisting of living or dead cells (prokaryotic and eukaryotic, including mammalian), viruses, bacteria, fungi, yeast, protozoan, microbes, parasites, and the like. As used herein, a pathogen is any disease causing organism or microorganism.

Exemplary mammalian cells include, but are not limited to, stem cells, cancer cells, progenitor cells, immune cells, blood cells, fetal cells, and the like.

Exemplary fungi and yeast include, but are not limited to, *Cryptococcus neoformans, Candida albicans, Candida tropicalis, Candida stellatoidea, Candida glabrata, Candida krusei, Candida parapsilosis, Candida guilliermondii, Candida viswanathii, Candida lusitaniae, Rhodotorula mucilaginosa, Aspergillus fumigatus, Aspergillus flavus, Aspergillus clavatus, Cryptococcus neoformans, Cryptococcus laurentii, Cryptococcus albidus, Cryptococcus gattii, Histoplasma capsulatum, Pneumocystis jirovecii* (or *Pneumocystis carinii*), *Stachybotrys chartarum*, and any combination thereof.

Exemplary bacteria include, but are not limited to: anthrax, *campylobacter*, cholera, diphtheria, enterotoxigenic *E. coli*, giardia, gonococcus, *Helicobacter pylori*, *Hemophilus influenza* B, *Hemophilus influenza* non-typable, meningococcus, pertussis, pneumococcus, salmonella, shigella, *Streptococcus* B, group A *Streptococcus*, tetanus, *Vibrio cholerae, yersinia, Staphylococcus, Pseudomonas* species, *Clostridia* species, *Myocobacterium tuberculosis, Mycobacterium leprae, Listeria monocytogenes, Salmonella typhi, Shigella dysenteriae, Yersinia pestis, Brucella* species, *Legionella pneumophila, Rickettsiae, Chlamydia, Clostridium perfringens, Clostridium botulinum, Staphylococcus aureus, Treponema pallidum, Haemophilus influenzae, Treponema pallidum, Klebsiella pneumoniae, Pseudomonas aeruginosa, Cryptosporidium parvum, Streptococcus pneumoniae, Bordetella pertussis, Neisseria meningitides*, and any combination thereof.

Exemplary parasites include, but are not limited to: *Entamoeba histolytica; Plasmodium* species, *Leishmania* species, *Toxoplasmosis, Helminths*, and any combination thereof.

Exemplary viruses include, but are not limited to, HIV-1, HIV-2, hepatitis viruses (including hepatitis B and C), Ebola virus, West Nile virus, and herpes virus such as HSV-2, adenovirus, dengue serotypes 1 to 4, ebola, enterovirus, herpes simplex virus 1 or 2, influenza, Japanese equine encephalitis, Norwalk, papilloma virus, parvovirus B19, rubella, rubeola, vaccinia, varicella, Cytomegalovirus, Epstein-Barr virus, Human herpes virus 6, Human herpes virus 7, Human herpes virus 8, Variola virus, Vesicular stomatitis virus, Hepatitis A virus, Hepatitis B virus, Hepatitis C virus, Hepatitis D virus, Hepatitis E virus, poliovirus, Rhinovirus, Coronavirus, Influenza virus A, Influenza virus B, Measles virus, Polyomavirus, Human Papilomavirus, Respiratory syncytial virus, Adenovirus, Coxsackie virus, Dengue virus, Mumps virus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B. Rotavirus C, Sindbis virus, Human T-cell Leukemia virus type-1, Hantavirus, Rubella virus, Simian Immunodeficiency viruses, and any combination thereof.

Exemplary contaminants found in non-biological fluids can include, but are not limited to microorganisms (e.g., *Cryptosporidium, Giardia lamblia*, bacteria, *Legionella*, Coliforms, viruses, fungi), bromates, chlorites, haloactic acids, trihalomethanes, chloramines, chlorine, chlorine dioxide, antimony, arsenic, mercury (inorganic), nitrates, nitrites, selenium, thallium, Acrylamide, Alachlor, Atrazine, Benzene, Benzo(a)pyrene (PAHs), Carbofuran, Carbon, etrachloride, Chlordane, Chlorobenzene, 2,4-D, Dalapon, 1,2-Dibromo-3-chloropropane (DBCP), o-Dichlorobenzene, p-Dichlorobenzene, 1,2-Dichloroethane, 1,1-Dichloroethylene, cis-1,2-Dichloroethylene, trans-1,2-Dichloroethylene, Dichloromethane, 1,2-Dichloropropane, Di(2-ethylhexyl) adipate, Di(2-ethylhexyl)phthalate, Dinoseb, Dioxin (2,3,7,8-TCDD), Diquat, Endothall, Endrin, Epichlorohydrin, Ethylbenzene, Ethylene dibromide, Glyphosate, Heptachlor, Heptachlor epoxide, Hexachlorobenzene, Hexachlorocyclopentadiene, Lead, Lindane, Methoxychlor, Oxamyl (Vydate), Polychlorinated, biphenyls (PCBs), Pentachlorophenol, Picloram, Simazine, Styrene, Tetrachloroethylene, Toluene, Toxaphene, 2,4,5-TP (Silvex), 1,2,4-Trichlorobenzene, 1,1,1-Trichloroethane, 1,1,2-Trichloroethane, Trichloroethylene, Vinyl chloride, and Xylenes.

Source Fluids

As used herein, the term "source fluid" refers to any flowable material that comprises the target component. Without wishing to be bound by theory, the source fluid can be liquid (e.g., aqueous or non-aqueous), supercritical fluid, gases, solutions, suspensions, and the like.

In some embodiments, the source fluid is a biological fluid. The terms "biological fluid" and "biofluid" are used interchangeably herein and refer to aqueous fluids of biological origin, including solutions, suspensions, dispersions, and gels, and thus may or may not contain undissolved particulate matter. Exemplary biological fluids include, but are not limited to, blood (including whole blood, plasma, cord blood and serum), lactation products (e.g., milk), amniotic fluids, sputum, saliva, urine, semen, cerebrospinal fluid, bronchial aspirate, perspiration, mucus, liquefied feces, synovial fluid, lymphatic fluid, tears, tracheal aspirate, and fractions thereof.

Another example of a group of biological fluids are cell culture fluids, including those obtained by culturing or fermentation, for example, of single- or multi-cell organisms, including prokaryotes (e.g., bacteria) and eukaryotes (e.g., animal cells, plant cells, yeasts, fungi), and including fractions thereof.

Yet another example of a group of biological fluids are cell lysate fluids including fractions thereof. For example, cells (such as red blood cells, white blood cells, cultured cells) may be harvested and lysed to obtain a cell lysate (e.g., a biological fluid), from which molecules of interest (e.g., hemoglobin, interferon, T-cell growth factor, interleukins) may be separated with the aid of the present invention.

Still another example of a group of biological fluids are culture media fluids including fractions thereof. For example, culture media comprising biological products (e.g., proteins secreted by cells cultured therein) may be collected and molecules of interest separated therefrom with the aid of the present invention.

In some embodiments, the source fluid is a non-biological fluid. As used herein, the term "non-biological fluid" refers to any aqueous, non-aqueous or gaseous sample that is not a biological fluid as the term is defined herein. Exemplary non-biological fluids include, but are not limited to, water, salt water, brine, organic solvents such as alcohols (e.g., methanol, ethanol, isopropyl alcohol, butanol etc. . . . ), saline solutions, sugar solutions, carbohydrate solutions, lipid solutions, nucleic acid solutions, hydrocarbons (e.g. liquid hydrocarbons), acids, gasolines, petroleum, liquefied samples (e.g., liquefied foods), gases (e.g., oxygen, $CO_2$, air, nitrogen, or an inert gas), and mixtures thereof.

In some embodiments, the source fluid is a media or reagent solution used in a laboratory or clinical setting, such as for biomedical and molecular biology applications. As used herein, the term "media" refers to a medium for maintaining a tissue or cell population, or culturing a cell population (e.g. "culture media") containing nutrients that maintain cell viability and support proliferation. The cell culture medium can contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art. The media can include media to which cells have been already been added, i.e., media obtained from ongoing cell culture experiments, or in other embodiments, be media prior to the addition of cells.

As used herein, the term "reagent" refers to any solution used in a laboratory or clinical setting for biomedical and molecular biology applications. Reagents include, but are not limited to, saline solutions, PBS solutions, buffer solutions, such as phosphate buffers, EDTA, Tris solutions, and the like. Reagent solutions can be used to create other reagent solutions. For example, Tris solutions and EDTA solutions are combined in specific ratios to create "TE" reagents for use in molecular biology applications.

Collection Fluids

As used herein, the term "collection fluid" refers to any flowable material that can be used for collecting the target component magnetic particle complexes Like source fluids, collection fluid can also be liquid (e.g., aqueous or non-aqueous), supercritical fluid, gases, solutions, suspensions, and the like.

Choice of collection fluid depends on the particular application and the source fluid. Generally, the collection fluid is chosen so that it is compatible with the source fluid and/or the target component-magnetic particle complex. As used herein, compatibility with the source fluid means that collection fluid has similar density, $C_p$, enthalpy, internal energy, viscosity, Joule-Thomson coefficient, specific volume, $C_v$, entropy, thermal conductivity, isotonicity, and/or surface tension to the source fluid. In some embodiments, the collection fluid is miscible with the source fluid. In some other embodiments, the collection fluid is not miscible with the source fluid.

In accordance with the invention, the collection fluid can be a fluid that is compatible with the source fluid and cleansing process. Thus, the collection fluid can be any fluid that will not contaminate the source fluid when mixed therein. In some embodiments, the collection fluid can be the same or similar composition as the source fluid. For example, where the source fluid is a biofluid, a compatible collection fluid such as an isotonic saline solution, a saline solution containing serum, such as fetal bovine serum, a physiological salt solution, a buffer, a cell culture media, or the like. Generally, the collection fluid should be isotonic compared to the biofluid to minimize diffusional mass transfer and osmotic damage to cells. Although collection fluid does not need to match the viscosity of the source fluid for proper operations, similar viscosities can minimize shear mixing. When the source fluid is a biological fluid, the collection fluid is generally a nontoxic fluid. Biocompatible or injectable solutions are desirable, especially for therapeutic applications involving human patients. In some embodiments, the collection fluid is a biological fluid, a biocompatible fluid or a biological fluid substitute.

As used herein, the term "biocompatible fluid" refers to any fluid that is appropriate for infusion into a subject's body, including normal saline and its less concentrated derivatives, Ringer's lactate, and hypertonic crystalloid solutions; blood and fractions of blood including plasma, platelets, albumin and cryoprecipitate; blood substitutes including hetastarch, polymerized hemoglobin, perfluorocarbons; LIPOSYN (lipid emulsion used for intravenous feeding); blood or serum components reconstituted with saline or sterile water, and combinations thereof.

In some embodiments, the collection fluid is selected from the group consisting of biological fluids, physiologically acceptable fluids, biocompatible fluids, water, organic solvents such as alcohols (e.g., methanol, ethanol, isopropyl alcohol, butanol etc. . . . ), saline solutions (e.g., isotonic saline solution), sugar solutions, hydrocarbons (e.g. liquid hydrocarbons), acids, and mixtures thereof. In some embodiments, the collection fluid is the source fluid without the target component. In some embodiments, the collection fluid is a gas such as oxygen, $CO_2$, air, nitrogen, or an inert gas.

Some Exemplary Uses for the Devices

The devices, systems, and methods described herein provide novel advantages for a variety of application including, but not limited to, therapeutic application (e.g., biofiltrations, toxin clearance, pathogen clearance, removal of cytokines or immune modulators), filtrations, enrichment, purifications, diagnostics, and the like.

In some embodiments, the devices, systems, and methods described herein are used to selectively separate target components from source fluids. For a non limiting example, the devices, systems, and methods provided herein can be used for separating cells, bioparticles, molecules and/or toxins from a biological fluid in treating a subject in need thereof.

Separated target components can be utilized for any purpose including, but not limited to, diagnosis, culture, sensitivity testing, drug resistance testing, pathogen typing or subtyping, PCR, NMR, mass spectroscopy, IR spectroscopy, and immunoassaying. Identification and typing of pathogens is critical in the clinical management of infectious diseases. Precise identity of a microbe is used not only to differentiate a disease state from a healthy state, but is also fundamental to determining whether and which antibiotics or other antimicrobial therapies are most suitable for treatment. Thus, pathogens separated from a subject's blood can be used for pathogen typing and sub-typing. Methods of pathogen typing are well known in the art and include using a variety of phenotypic features such as growth characteristics; color; cell or colony morphology; antibiotic susceptibility; staining; smell; and reactivity with specific antibodies, and molecular methods such as genotyping by hybridization of specific nucleic acid probes to the DNA or RNA; genome sequencing; RFLP; and PCR fingerprinting.

In PCR finger printing, the size of a fragment generated by PCR is used as an identifier. In this type of assay, the primers are targeted to regions containing variable numbers of tandem repeated sequences (referred to as VNTRs an eukaryotes). The number of repeats, and thus the length of the PCR amplicon, can be characteristic of a given pathogen, and co-amplification of several of these loci in a single reaction can create specific and reproducible fingerprints, allowing discrimination between closely related species. In cases where organisms are very closely related, the target of the amplification may not display a size difference, and the amplified segment must be further probed to achieve more precise identification. This may be accomplished by using the interior of the PCR fragment as a template for a sequence-specific ligation event.

The methods, systems, and devices described herein can also be used to determine if there are different sub-populations of a pathogen or a combination of different pathogens present in an infected subject. The ability to quickly determine subtypes of pathogens can allow comparisons of the clinical outcomes from infection by the different pathogen subtypes, and from infection by multiple types in a single individual. In many cases, a pathogen subtype has been associated with differential efficacy of treatment with a specific drug. For example, HCV type has been associated with differential efficacy of treatment with interferon. Pre-screening of infected individuals for the pathogen subtype type can allow the clinician to make a more accurate diagnosis, and to avoid costly but fruitless drug treatment.

As used herein, removing or separating target components means that the amount of the target component is reduce by at least 5%, 10%, 20%, 30%, 40%, 50%, 60%, 70%, 75%, 80%, 85%, 90%, 95%, 100% (completely reduction) in the source fluid.

In some embodiments, the devices, systems, and methods provided herein are used to remove sepsis related target components from the blood of a subject in need thereof. As used herein, sepsis related target components refer to any molecule or bioparticle that can contribute to development of sepsis in a subject.

As used herein, "sepsis" refers to a body or subject's response to a systemic microbial infection. Sepsis is the leading cause of death of immunocompromised patients, and is responsible for over 200,000 deaths per year in the United States. The onset of sepsis occurs when rapidly growing infectious agents saturate the blood and overcome a subject's immunological clearance mechanisms. Most existing therapies are ineffective, and subjects can die because of clot formation, hypoperfusion, shock, and multiple organ failure.

In some embodiments, the devices, systems, and methods provided herein are used to in combination with conventional therapies for treating a subject in need thereof. For example, the devices, systems, and methods provided herein are used in conjunction with conventional therapies for sepsis treatment, such as fungicides. In another example, the devices, systems, and methods described herein are used for treating a subject having a cancer. The method comprising removing cancer cells from a biological fluid obtained from the subject, and providing an additional treatment including, but not limited to, chemotherapy, radiation therapy, steroids, bone marrow transplants, stem cell transplants, growth factor administration, ATRA (all-trans-retinoic acid) administration, histamine dihydrochloride (Ceplene) administration, interleukin-2 (Proleukin) administration, gemtuzumab ozogamicin (Mylotarg) administration, clofarabine administration, farnesyl transferase inhibitor administration, decitabine administration, inhibitor of MDR1 (multidrug-resistance protein) administration, arsenic trioxide administration, rituximab administration, cytarabine (ara-C) administration, anthracycline administration (such as daunorubicin or idarubicin), imatinib administration, dasatanib administration, nilotinib administration, purine analogue (such as fludarabine) administration, alemtuzumab (anti-CD52) administration, (fludarabine with cyclophosphamide), fludarabine administration, cyclophosphamide administration, doxorubicin administration, vincristine administration, prednisolone administration, lenalidomide administration, flavopiridol administration, or any combination therein. In some embodiments, the devices, systems, and methods provided herein are used for treating a subject in need thereof without providing any other therapy to the subject. For example, the devices, systems, and methods provided herein are used for sepsis treatment, pathogen and/or toxin clearance from biological fluids, of a subject in need thereof.

In some embodiments, the devices, systems, and methods described herein are used to purify or enrich a target component from a source fluid. For example, the devices, systems, and methods described herein can be used to purify products of chemical reactions or molecules being produced in a cell culture.

Isolation and Enrichment of Rare Populations of Cells from Source Fluids

In some aspects of the invention, the methods, devices, and systems described herein can be used for isolating and enriching for rare cell populations, such as stem cells, progenitor cells, cancer cells, or fetal cells from source fluids. Because the entire blood volume of a patient can be circulated through the device, low frequency populations can be identified using this method. Such populations of cells may represent a small fraction of cells present in a source fluid, and may be otherwise difficult to isolate or enrich for.

A source fluid from which rare populations of cells can be isolated from or enriched for can be any fluid sample in which such cells may be present. In some embodiments, the source fluid is a biological sample that is found naturally in the fluid form, such as whole blood, plasma, serum, amniotic fluid, cord blood, lymph fluid, cerebrospinal fluid, urine, sputum, pleural fluid, tears, breast milk, nipple aspirates, and saliva. In other embodiments, the biofluid sample is a fluid sample prepared from a solid or semi-solid tissue, organ, or other biological sample from which rare cell populations may be isolated or enriched for. In such embodiments, single-cell populations may be prepared from a tissue or organ, and resuspended in a buffer, such as saline solutions containing serum, for use in the methods and devices described herein. Such single-cell suspensions may be prepared using any method known to one of skill in the art, such as manual methods using slides, enzyme treatment, or tissue dissociators. Tissues and organs from which single-cell suspensions may be prepared for use in the methods and devices described herein, include, but are not limited to, bone marrow, thymus, stool, skin sections, spleen tissue, pancreatic tissue, cardiac tissue, lung tissue, adipose tissue, connective tissue, sub-epithelial tissue, epithelial tissue, liver tissue, kidney tissue, uterine tissue, respiratory tissues, gastrointestinal tissue, genitourinary tract tissue and cancerous tissues.

In one or more embodiments of the aspects, rare populations of cells, such as stem cells, can be identified for isolation and enrichment using the methods, devices, and systems described herein by one or more markers, such as cell-surface markers, specific for the rare cell population. Accordingly, in such embodiments, magnetic particles bound to or conjugated to a binding molecule specific for one or more of the markers present on or in the rare cell population can be used. In some embodiments, the affinity molecule is an antibody or antigen-binding fragment specific for a marker. In some embodiments, one or more affinity molecules specific for one or more markers found on or in a rare cell population are conjugated to magnetic particles. For example, one magnetic particle can be conjugated to multiple different affinity molecules, where each affinity molecule is specific for a different marker associated with the rare cell population. In another example, a combination of magnetic particles is used, where each magnetic particle is conjugated or bound to affinity molecules specific for a single cell marker, and a combination of such particles is used to isolate or enrich for a rare cell population. In one or more embodiments, the rare cell population is a stem cell or progenitor cell population.

Exemplary cell markers can include, but are not limited to, one or more of the following markers: c-Myc, CCR4, CD15 (SSEA-1, Lewis X), CD24, CD29 (Integrin β1), CD30, CD49f (Integrin α6), CD9, CDw338 (ABCG2), E-Cadherin, Nanog, Oct3/4, Smad2/3, Sox2, SSEA-3, SSEA-4, STAT3 (p5727), STAT3 (pY705), STAT3, TRA-1-60, TRA-1-81, CD117 (SCF R, c-kit), CD15 (SSEA-1, Lewis X), VASA (DDX4), CDX2, Cytokeratin 7, Trop-2, GFAP, S100B, Nestin, Notch1, CD271 (p75, NGFR/NTR), CD49d (Integrin α4), CD57 (HNK-1), MASH1, Neurogenin 3, CD146 (MCAM, MUC18), CD15s (Sialyl Lewis x), CD184 (CXCR4), CD54 (ICAM-1), CD81 (TAPA-1), CD95 (Fas/APO-1), CDw338 (ABCG2), Ki-67, Noggin, Sox1, Sox2, Vimentin, α-Synuclein (pY125), α-Synuclein, CD112, CD56 (NCAM), CD90 (Thy-1), CD90.1 (Thy-1.1), CD90.2 (Thy-1.2), ChAT, Contactin, Doublecortin, GABA A Receptor, Gad65, GAP-43 (Neuromodulin), GluR delta 2, GluR2, GluR5/6/7, Glutamine Synthetase, Jagged1, MAP2 (a+b), MAP2B, mGluR1 alpha, mGluR1, N-Cadherin, Neurofilament NF-H, Neurofilament NF-M, Neuropilin-2, Nicastrin, P-glycoprotein, p150 Glued, Pax-5, PSD-95, Serotonin Receptor 5-HT 2AR, Serotonin Receptor 5-HT 2BR, SMN, Synapsin I, Synaptophysin, Synaptotagmin, Syntaxin, Tau, TrkB, Tubby, Tyrosine Hydroxylase, Vimentin, CD140a (PDGFR α), CD44, CD44H (Pgp-1, H-CAM), CRABP2, Fibronectin, Sca-1 (Ly6A/E), β-Catenin, GATA4, HNF-1β (TCF-2), N-Cadherin, HNF-1α, Tat-SF1, CD49f (Integrin α6), Gad67, Neuropilin-2, CDX2, CD31 (PECAM1), CD325 (M-Cadherin), CD34 (Mucosialin, gp 105-120), NF-YA, CD102, CD105 (Endoglin), CD106 (VCAM-1), CD109, CD112, CD116 (GM-CSF Receptor), CD117 (SCF R, c-kit), CD120a (TNF Receptor Type I), CD120b (TNF Receptor Type II), CD121a (IL-1 Receptor, Type I/p80), CD124 (IL-4 Receptor α), CD141 (Thrombomodulin), CD144 (VE-cadherin), CD146 (MCAM, MUC18), CD147 (Neurothelin), CD14, CD151, CD152 (CTLA-4), CD157, CD166 (AL-CAM), CD18 (Integrin β2 chain, CR3/CR4), CD192 (CCR2), CD201 (EPCR), CD202b (TIE2) (pY1102), CD202b (TIE2) (pY992), CD202b (TIE2), CD209, CD209a (CIRE, DC-SIGN), CD252 (OX-40 Ligand), CD253 (TRAIL), CD262 (TRAIL-R2, DR5), CD325 (M-Cadherin), CD36, CD45 (Leukocyte Common Antigen, Ly-5), CD45R (B220), CD49d (Integrin α4), CD49e (Integrin α5), CD49f (Integrin α6), CD54 (ICAM-1), CD56 (NCAM), CD62E (E-Selectin), CD62L (L-Selectin), CD62P (P-Selectin), CDw93 (C1qRp), Flk-1 (KDR, VEGF-R2, Ly-73), HIF-1α, IP-10, α-Actinin, Annexin VI, Caveolin-2, Caveolin-3, CD66, CD66c, Connexin-43, Desmin, Myogenin, N-Cadherin, CD325 (E-Cadherin), CD10, CD124 (IL-4 Receptor α), CD127 (IL-7 Receptor α), CD38, HLA-DR, Terminal Transferase (TdT), CD41, CD61 (Integrin β3), CD11c, CD13, CD114 (G-CSF Receptor), CD71 (Transferrin Receptor), PU.1, TER-119/Erythroid cells (Ly-76), CaM Kinase IV, CD164, CD201 (EPCR), CDw338 (ABCG2), CDw93 (C1qRp), MRP1, Notch1, P-glycoprotein, WASP (Wiskott-Aldrich Syndrome Protein), Acrp30 (Adiponectin), CD151, β-Enolase (ENO-3), Actin, CD146 (MCAM, MUC18), MyoD, IGFBP-3, CD271 (p75, NGFR/NTR), CD73 (Ecto-5'-nucleotidase), and TAZ.

As used herein, the terms "isolate" and "methods of isolation," refers to a process whereby a target component is removed from a source fluid. In reference to isolation of cells, the terms "isolate" and "methods of isolation," refers to a process whereby a cell or population of cells is removed from a subject or fluid sample in which it was originally found, or a descendant of such a cell or cells. The term "isolated population" with respect to an isolated population of cells, as used herein, refers to a population of cells that has been removed and separated from a source fluid, or a mixed or heterogeneous population of cells found in such a sample. Such a mixed population includes, for example, a population of peripheral blood mononuclear cells obtained from isolated blood, or a cell suspension of a tissue sample, such as a single-cell suspension prepared from the spleen. In one or more embodiments, an isolated population is a substantially pure population of cells as compared to the heterogeneous population from which the cells were isolated or enriched from. In one or more embodiments of this aspect and all aspects described herein, the isolated population is an isolated population of progenitor cells. In one or more embodiments, an isolated cell or cell population, such as a population of progenitor cells, is further cultured in vitro, e.g., in the presence of growth factors or cytokines, to further expand the number of cells in the isolated cell population or substantially pure cell population. Such culture can be performed using any method known to one of skill in the art. In one or more embodiments, the isolated or substantially pure progenitor cell populations obtained by the methods disclosed herein are later introduced into a second subject, or re-introduced into the subject from which the cell population was originally isolated (e.g., allogenic transplantation).

As used herein, the term "substantially pure," with respect to a particular cell population, refers to a population of cells that is at least about 75%, at least about 80%, at least about 85%, at least about 90%, at least about 95%, at least about 98%, or at least about 99% pure, with respect to the cells making up a total cell population. In other words, the terms "substantially pure" or "essentially purified", with regard to a population of progenitor cells isolated using the methods as disclosed herein, refers to a population of progenitor cells that contain fewer than about 25%, fewer than about 20%, fewer than about 15%, fewer than about 10%, fewer than about 9%, fewer than about 8%, fewer than about 7%, fewer than about 6%, fewer than about 5%, fewer than about 4%, fewer than about 4%, fewer than about 3%, fewer than about 2%, fewer than about 1%, or less than 1%, of cells that are not progenitor cells as defined by the terms herein.

In some embodiments, rare populations of cells are enriched for using the methods, systems, and devices described herein. The terms "enriching" or "enriched" are used interchangeably herein and mean that the yield (fraction) of cells of one type, such as progenitor cells, is increased by at least 15%, by at least 20%, by at least 25%, by at least 30%, by at least 35%, by at least 40%, by at least 45%, by at least 50%, by at least 55%, by at least 60%, by at least 65%, by at least 70%, or by at least 75%, over the fraction of cells of that type in the starting biofluid sample, such as a culture or human whole blood.

Removal of Cancer Cells from Source Fluids

The methods, systems, and devices described herein can also provide novel advantages for use in therapies for cancer treatment, such as removal of cancer cells present in source fluids obtained from a patient or subject at risk for or having a cancer, such as hematological malignancies or metastatic cells from other organ sites. In one or more embodiments, the cancer cell is an ALL, B-CLL, CML, AML cancer cell, or a cancer cells from the breast, lung, kidney, brain, spinal cord, liver, spleen, blood, bronchi, central nervous system, cervix, colon, rectum and appendix, large intestine, small intestine, bladder, testicles, ovaries, pelvis, lymph nodes, esophagus, uterus, bile ducts, pancreas, gall bladder, uvea, retina, upper aerodigestive tract (e.g., lip, oral cavity (mouth), nasal cavity, paranasal sinuses, pharynx, and larynx), ovaries, parathyroid glands, pineal glands, pituitary gland, prostate, connective tissue, skeletal muscle, salivary gland, thyroid gland, thymus gland, urethra, or vulva.

Hematological malignancies, as used herein, refers to those types of cancer that affect blood, bone marrow, and lymph nodes. As the three are intimately connected through the immune system, a disease affecting one of the three will often affect the others as well: although lymphoma is technically a disease of the lymph nodes, it often spreads to the bone marrow, affecting the blood and occasionally produces a paraprotein.

Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are conditions that arise from the lymphoid line, while acute and chronic myelogenous leukemia, myelodysplastic syndromes and myeloproliferative diseases involve cancer cells that are myeloid in origin.

In some embodiments of the aspects, subject having or at risk for a cancer, such as ALL, B-CLL, CML or AML, is treated using the methods, devices, and systems described herein. In such embodiments, the methods, devices, and systems described herein are used to remove cancer cells from a source fluid obtained from a subject having or at risk for a cancer. some embodiments, the source fluid is a biological fluid such as blood or bone marrow obtained from the subject.

In some embodiments, binding molecules specific for one or more markers, such as cell-surface markers, specific for the cancer cell population are used to remove cancer cells from a source fluid obtained from a subject. Accordingly, in such embodiments, magnetic particles bound to or conjugated to binding molecules specific for one or more of the markers present on or in the cancer cell population can be used. In some embodiments, the binding molecule is an antibody or antigen-binding fragment specific for a marker present on or in the cancer cell population. For example, in some embodiments, a monoclonal antibody specific for a B cell light chain present only on CLL cells can be bound to or conjugated to magnetic particles, and such conjugated magnetic particles can be contacted with a fluid sample from a subject having CLL to remove CLL cells, using the methods, devices, and systems described herein.

In some embodiments, one or more binding molecules specific for one or more markers found on or in a cancer cell population are conjugated to magnetic particles. For example, one magnetic particle can be conjugated to multiple different affinity molecules, where each binding molecule is specific for a different marker associated with the cancer cell population. In another example, a combination of magnetic particles is used, where each magnetic particle is conjugated or bound to one type of binding molecule, such as an antibody specific for a cancer cell surface marker, and a combination of such particles is used to isolate or enrich for the cancer cell population.

Exemplary cancer markers include, but are not limited to, CD19, CD20, CD22, CD33, CD52, monotypic surface IgM, CD10, Bcl-6, CD79a, CD5, CD23, and Terminal deoxytransferase (TdT). Any additional markers that are identified as being unique to or increased upon cancer cells, such as leukemias, are also included within the scope of the methods, devices, and systems described herein.

Other cancer antigens useful within the scope of the methods, devices, and systems described herein, include, for example PSA, Her-2, Mic-1, CEA, PSMA, mini-MUC, MUC-1, HER2 receptor, mammoglobulin, labyrinthine, SCP-1, NY-ESO-1, SSX-2, N-terminal blocked soluble cytokeratin, 43 kD human cancer antigens, PRAT, TUAN, Lb antigen, carcinoembryonic antigen, polyadenylate polymerase, p53, mdm-2, p21, CA15-3, oncoprotein 18/stathmin, and human glandular kallikrein), melanoma antigens, and the like.

In other embodiments of the aspects described herein, the methods and systems comprise removing target cancer cells from a source fluid obtained from a subject having or at risk for cancer and further comprise subjecting the removed cancer cells to genetic analyses to identify the cause or nature of the cancer. Such identification can enable enhanced treatment modalities and efficacy. Without wishing to be bound by theory, this can further allow the methods, devices and systems described herein to be used in personalized medicine treatments. For example, such genetic analyses on the removed cells can be used to identify which of the causal chromosomal translocation events involved in AML predisposition is causing a subject's AML, such as identifying that the translocation is occurring between chromosome 10 and 11.

The terms "subject," "patient," and "individual" are used interchangeably herein, and refer to an animal, for example a human, requiring treatment for a cancer, such as a leukemia. For treatment of disease states which are specific for a specific animal such as a human subject, the term "subject" refers to that specific animal. The terms "non-human animals" and "non-human mammals" are used interchangeably herein, and include mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like are also encompassed in the term subject.

As used herein, "cancer" refers to any of various malignant neoplasms characterized by the proliferation of neoplastic cells that tend to invade surrounding tissue and metastasize to new body sites and also refers to the pathological condition characterized by such malignant neoplastic growths. The blood vessels provide conduits to metastasize and spread elsewhere in the body. Upon arrival at the metastatic site, the cancer cells then work on establishing a new blood supply network. Encompassed in the methods disclosed herein are subjects that are treated for cancer, including but not limited to all types of carcinomas and sarcomas, such as those found in the anus, bladder, bile duct, bone, brain, breast, cervix, colon/rectum, endometrium, esophagus, eye, gallbladder, head and neck, liver, kidney, larynx, lung, mediastinum (chest), mouth, ovaries, pancreas, penis, prostate, skin, small intestine, stomach, spinal marrow, tailbone, testicles, thyroid and uterus. The types of carcinomas include papilloma/carcinoma, choriocarcinoma, endodermal sinus tumor, teratoma, adenoma/adenocarcinoma, melanoma, fibroma, lipoma, leiomyoma, rhabdomyoma, mesothelioma, angioma, osteoma, chondroma, glioma, lymphoma/leukemia, squamous cell carcinoma, small cell carcinoma, large cell undifferentiated carcinomas, basal cell carcinoma and sinonasal undifferentiated carcinoma. The types of sarcomas include soft tissue sarcoma such as alveolar soft part sarcoma, angiosarcoma, dermatofibrosarcoma, desmoid tumor, desmoplastic small round cell tumor, extraskeletal chondrosarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, synovial sarcoma, and Askin's tumor, Ewing's sarcoma (primitive neuroectodermal tumor), malignant hemangioendothelioma, malignant schwannoma, osteosarcoma, and chondrosarcoma.

The methods, devices and systems described herein are also useful in determining patient specific and general response of cancer patients to therapies (radiation or chemical). For example, circulating tumor cells from a subject can be isolated and analyzed before and after onset of a treatment regime. The methods, devices and systems described herein can also be used to determine cancer staging and/or early diagnosis of malignancy. For example, the magnetic particles can be tagged with a label for easy detection of free and cell bound particles. Separated cells can also analyzed for stage specific markers. The stage of a cancer is a descriptor (usually numbers I to IV) of how much the cancer has spread. The stage often takes into account the size of a tumor, how deeply it has penetrated, whether it has invaded adjacent organs, how many lymph nodes it has metastasized to (if any), and whether it has spread to distant organs. Staging of cancer is important because the stage at diagnosis is the most powerful predictor of survival, and treatments are often changed based on the stage. Correct staging is critical because treatment is directly related to disease stage. Incorrect staging can lead to improper treatment, and material diminution of patient survivability. Oversight of one cell can mean mistagging and lead to serious, unexpected spread of cancer.

As used herein, the terms "treat" or "treatment" or "treating" refer to both therapeutic treatment and prophylactic or preventative measures, wherein the object is to prevent or slow the development of the disease. Without wishing to be limited by examples, if the disease is cancer, the slowing of the development of a tumor, the spread of cancer, or reducing at least one effect or symptom of a condition, disease or disorder associated with inappropriate proliferation or a cell mass, for example cancer would be considered a treatment. Treatment is generally "effective" if one or more symptoms or clinical markers are reduced as that term is defined herein. Alternatively, treatment is "effective" if the progression of a disease is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with cancer, as well as those likely to develop secondary tumors due to metastasis.

In some aspects of the invention, the methods, devices, and systems described herein can be used for analysis and for detecting the presence of target components in a source fluid. After separation form the source fluid, the target component can be analyzed using any method known in the art for detection of such a target component. For example, the target component can be tagged with a label such as dyes, antibodies, molecules which bind with the target component and easily detectable, or molecules which bind with the target component and are conjugated with a label. Alternatively, other methods such as optical techniques, e.g., microscopy, phase contrast imaging, etc. can be employed for detection of target components.

The collection fluid can be analyzed while the collection fluid is still in the collection microchannel or a portion of the collection fluid removed and the removed portion analyzed for presence of the target component. In some embodiments, magnetic particles from the collection fluid can be separated from the collection fluid and analyzed for presence of bound target components. In some embodiments, the outlet port of the collection channel can be connected to an inline or on-chip diagnostic device, used to analyze the target components. In this embodiment, the inline or on-chip diagnostic device can use magnetic field gradients to control the movement of the magnetically bound target components in order to subject them to inline analysis and testing and, for example, to provide detection of detection of low concentrations of pathogens in relatively small volumes of biofluids. For example, magnetic field gradients can be used to separate or isolate the magnetically bound target components from the collection fluid and then analyzed using one or more of dyes, antibodies, non-labeled optical or solid-state detection techniques.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

In a prototype system, six NiFeB magnets (6 mm×2 mm×2 cm; w×h×l) were stacked 2×3 with alternating magnetic field directions, such that the overall dimensions were (18 mm×4 mm×2 cm; w×h×l), before placing them adjacent to the microfluidic device. Alternatively, one NiFeB magnet or an electromagnet with appropriate field concentrator that can cover all the throughholes and exert the sufficient magnetic pulling forces (field gradient) could have been used. In the case of using permanent magnets, it was critical that the widest face of the magnets was facing the channels below because this face (18 mm×2 cm; w×l) has the highest magnetic flux and thus pulling strength. Using a six-magnet configuration, the magnetic field strength was approximately 50 mT-100 mT at a distance of 3 mm-5 mm, which was at the distance of the flowing fluid (blood) layer. The third layer of PDMS had the same network of channels facing down, but was connected to the blood fluid channels only by the transfer channels in the middle of the device (five 2 mm holes per channel). In the experiment, the dimensions of the channels were 1.5 mm×0.1 μm×2 cm (w×h×l).

Blood flow was actuated by a 12-head low-pulsatility peristaltic pump downstream of the device, and the collection fluid flow and timing was manually controlled by a 10 mL syringe filled with saline solution upstream of the microfluidic device. The pathogens collected in the effluent carrier fluid were analyzed using a previously developed flow cytometry assay that could accurately and simultaneously quantify the concentrations of opsonized pathogens, lone pathogens, and excess beads (C. W. Yung, et al., *Lab on a Chip* (2009) 9: 1171-1177).

A single four-channel device with one through-hole (transfer channel) per channel was able to clear 55% of all opsonized pathogens (op) and 92% of all excess beads (xb) in a 10 mL volume of human whole blood in a single pass at a rate of 12 mL/hr. A microfluidic device with five throughholes per channel was able to clear 85% of opsonized pathogens and 86% of excess beads (12 mL/hr; 15 mL total). When two devices were assembled in series, as shown in example configuration in FIG. 3B, the multiplexed system was able to clear 60% of opsonized pathogens and 58% of excess beads at a higher flow rate (18 mL/hr) from a much larger total blood volume (100 mL), without any evidence of clotting or flow restriction. The relatively reduced separation efficiency was most likely due to the 1.5-fold increase in flow rate, and it was concluded that the system configuration could be further optimized.

Figure 7:
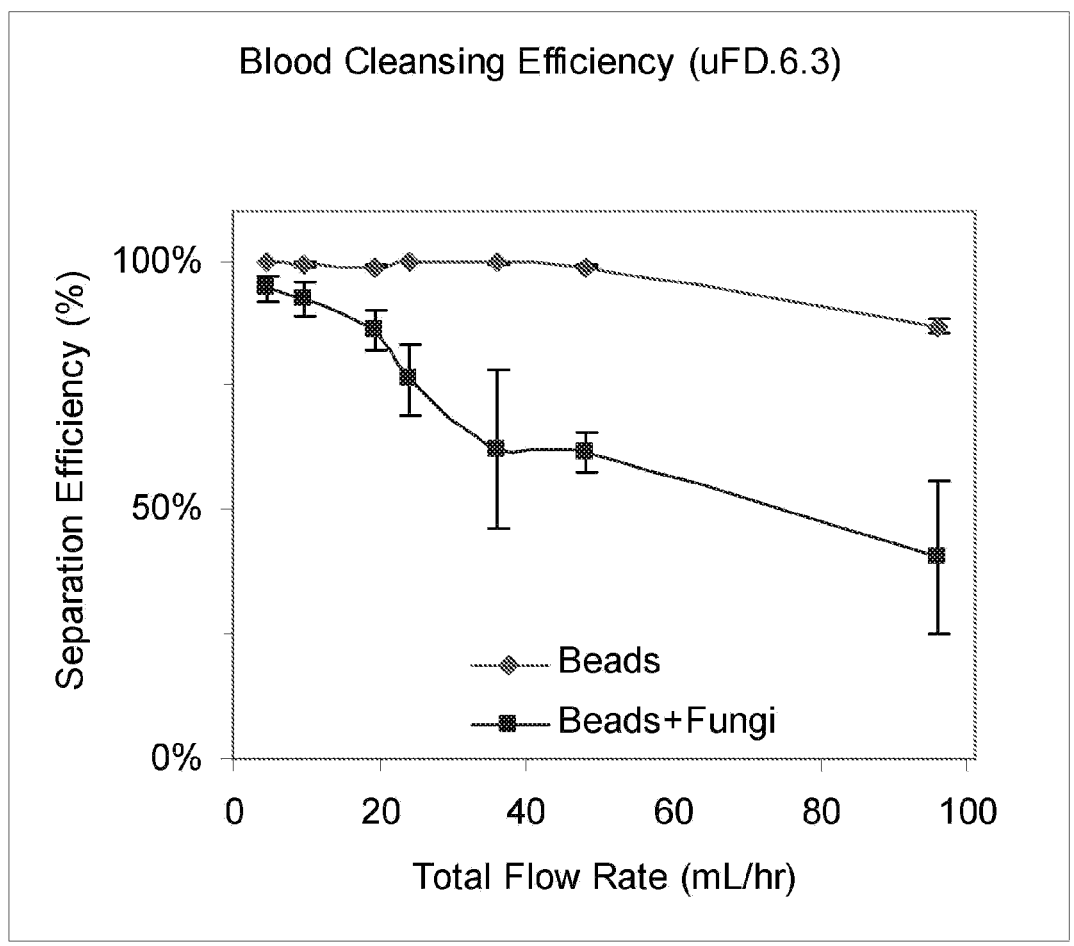
FIG. 7 shows a graph of the separation efficiency of one embodiment of the invention.

Utilizing a similar design with 16 parallel channels, we tested a range of process flow rates (4.8-96.0 mL/hr). At a blood flow rate of 5 mL/hr, the device was able to separate ~95% of bound fungi and ~100% of excess beads as shown in FIG. 7 and Table 1 below.

TABLE 1

| Blood Flow mL/hr | Separation Efficiency | |
|---|---|---|
| 4.8 | 99.8% | 94.3% |
| 9.6 | 99.4% | 92.3% |
| 19.2 | 98.7% | 85.9% |
| 24.0 | 99.8% | 76.2% |
| 36.0 | 99.7% | 62.0% |
| 48.0 | 98.8% | 61.6% |
| 96.0 | 86.7% | 40.7% |

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

What is claimed is:

1. A microfluidic device comprising:
a source microchannel connected between a source inlet and a source outlet;
a collection microchannel connected between a collection inlet and a collection outlet;
at least one transfer channel connecting the source microchannel and the collection microchannel;
a magnetic field source disposed adjacent to the collection microchannel and configured to apply a magnetic field gradient to a fluid flowing in the source microchannel and to cause target components in the source microchannel to migrate into at least one transfer microchannel, wherein the magnetic field source is positioned over said at least one transfer channel.

2. The microfluidic device of claim 1, further comprising a fluid source connected to the source microchannel and delivering a source fluid to the source channel, the source fluid including target components to be removed from the source fluid; and a collection fluid source connected to the collection microchannel and delivering a collection fluid to the collection microchannel to fill the collection microchannel and the transfer microchannel, and to flush the target components from the collection microchannel.

3. The microfluidic device of claim 2, wherein the source fluid is a biological fluid selected from the group consisting of blood, plasma, serum, lactation products, amniotic fluids, sputum, saliva, urine, semen, cerebrospinal fluid, bronchial aspirate, perspiration, mucus, liquefied stool sample, synovial fluid, lymphatic fluid, tears, tracheal aspirate, and any mixtures thereof.

4. The microfluidic device of claim 2, wherein the source fluid is a non-biological fluid selected from the group consisting of water, organic solvents, saline solutions, sugar solutions, carbohydrate solutions, lipid solutions, nucleic acid solutions, hydrocarbons, acids, gasoline, petroleum, liquefied foods, gases, and any mixtures thereof.

5. The microfluidic device of claim 2, wherein the collection fluid is selected from the group consisting of water, organic solvents, saline solutions, isotonic saline, a biological fluid, a biocompatible fluid, a biological fluid substitute, sugar solutions, carbohydrate solutions, lipid solutions, nucleic acid solutions, hydrocarbons, acids, gasoline, petroleum, liquefied foods, gases, and any mixtures thereof.

6. The microfluidic device of claim 1, wherein the target component is attracted or repelled by a magnetic field.

7. The microfluidic device of claim 1, wherein the target component is bound to a particle that is attracted or repelled by a magnetic field.

8. The microfluidic device of claim 7, wherein the particle is of size in range from 1 nm to 100 µm.

9. The microfluidic device of claim 1, wherein the at least one transfer channel is oriented at an angle of less than 90 degrees to the source microchannel.

10. The microfluidic device of claim 1, wherein the source microchannel and the collection microchannel each have a length of 1 mm to 10 cm, a width of 0.1 mm to 10 mm and a depth of 0.1 mm to 2 mm.

11. The microfluidic device of claim 1, wherein the microfluidic device is fabricated from a biocompatible material.

12. The microfluidic device according to claim 1 further comprising an inline diagnostic device connected to the collection outlet adapted to analyze the target components.

13. A method of separating a target component from a source fluid, the method comprising:
  a. providing a microfluidic device having a source microchannel, a collection microchannel, and at least one transfer channel connecting the source microchannel to the collection microchannel, wherein a magnetic field source is positioned over said at least one transfer channel;
  b. causing the source fluid to flow through the source microchannel, wherein the source fluid includes the target component to be removed/separated, wherein the target component is attracted or repelled by a magnetic field;
  c. providing a collection fluid in the collection microchannel; and
  d. applying a magnetic field to the source fluid in the source channel, whereby the target components migrate into the transfer channel.

14. The method of claim 13, further comprising causing the collection fluid to flow through the collection channel, wherein the target components in the collection fluid are removed from the collection microchannel.

15. The method of claim 13, wherein the target component is selected from the group consisting of hormones, cytokines, proteins, peptides, prions, lectins, oligonucleotides, molecular or chemical toxins, cells, bioparticles, pathogens, and any combination thereof.

16. The method of claim 13, further comprising adding particles into the source fluid before or after initiating flow of the source fluid through the source microchannel, wherein the particles are attracted or repelled by a magnetic field gradient.

17. The method of claim 13 further comprising collecting the collection fluid containing the target component in a collection fluid collector, removing at least one target component from the collection fluid collector and analyzing the removed target component using one or more of the processes selected from the group consisting of immunostaining, culturing, PCR, mass spectrometry and antibiotic sensitivity testing.

18. The method of claim 13 further comprising detecting presence of the target component in the collection fluid.

19. A microfluidic system comprising:
  a source microchannel connected between a source inlet and a source outlet;
  a collection microchannel connected between a collection inlet and a collection outlet;
  at least one transfer channel connecting the source microchannel and the collection microchannel;
  a magnetic source disposed adjacent to the collection microchannel and configured to apply a magnetic field gradient to a fluid flowing in the source microchannel and to cause target components in the source microchannel to migrate into at least one transfer channel, wherein the magnetic field source is positioned over said at least one transfer channel;
  a fluid source connected to the source microchannel, adapted to deliver a source fluid to the source microchannel, the source fluid including target components to be removed from the source fluid, and,
  a collection fluid source connected to the collection microchannel, adapted to deliver a collection fluid to the collection microchannel to draw the target components from the transfer microchannel into the collection microchannel and flush the target components from the collection channel
  a source pump, connected to the source microchannel, and adapted to pump source fluid into the source microchannel;
  a source mixer, connected to the source microchannel and the fluid source, and adapted to mix the source fluid with magnetic particles;
  a collection pump, connected to the collection microchannel and the collection fluid source, and adapted to pump collection fluid into the collection microchannel; and
  a controller, having a processor and associated memory, and being coupled to the source pump to control the flow of source fluid through the source microchannel and being coupled to the collection pump to control the flow of collection fluid through the collection microchannel.

20. The microfluidic system according to claim 19 further comprising an inline diagnostic device, connected to the collection outlet, adapted to analyze at least one of the target components in the collection fluid.

* * * * *

UNITED STATES PATENT AND TRADEMARK OFFICE
CERTIFICATE OF CORRECTION

PATENT NO. : 9,156,037 B2
APPLICATION NO. : 13/144572
DATED : October 13, 2015
INVENTOR(S) : Chong Wing Yung et al.

It is certified that error appears in the above-identified patent and that said Letters Patent is hereby corrected as shown below:

IN THE SPECIFICATION

In column 1, lines 18-21, the paragraph "The subject matter described herein was made with support under grant number No. W81XWH-05-1-0115 awarded by the United States Department of Defense. The United States government has certain rights in the claimed subject matter." should read --This invention was made with government support under W81XWH-09-2-0001 and W81XWH-05-1-0115 awarded by the U.S. Department of Defense/U.S. Army MRMC. The government has certain rights in the invention.--

Signed and Sealed this
Eighth Day of March, 2016

Michelle K. Lee
*Director of the United States Patent and Trademark Office*